(12) United States Patent
Shelton, IV

(10) Patent No.: US 8,057,508 B2
(45) Date of Patent: *Nov. 15, 2011

(54) SURGICAL INSTRUMENT INCORPORATING AN ELECTRICALLY ACTUATED ARTICULATION LOCKING MECHANISM

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1281 days.

This patent is subject to a terminal disclaimer.

(21) Appl. No.: 11/092,053

(22) Filed: Mar. 29, 2005

(65) Prior Publication Data

US 2006/0025810 A1 Feb. 2, 2006

Related U.S. Application Data

(60) Provisional application No. 60/591,694, filed on Jul. 28, 2004.

(51) Int. Cl.
*A61B 17/50* (2006.01)
(52) U.S. Cl. ...................................................... 606/208
(58) Field of Classification Search .................. 606/205, 606/207, 208; 227/175.1–182.1
See application file for complete search history.

(56) References Cited

U.S. PATENT DOCUMENTS

| | | | |
|---|---|---|---|
| 2,711,461 A | 6/1955 | Happe | |
| 4,473,077 A | 9/1984 | Noiles et al. | |
| 4,543,090 A | 9/1985 | McCoy | |
| 4,554,064 A | 11/1985 | McClintock et al. | |
| 4,566,620 A | 1/1986 | Green et al. | |
| 4,601,705 A | 7/1986 | McCoy | |
| 4,753,223 A | 6/1988 | Bremer | |
| 4,892,545 A | 1/1990 | Day et al. | |
| 5,031,814 A | 7/1991 | Tompkins et al. | |
| 5,040,715 A | 8/1991 | Green et al. | |
| 5,071,052 A | 12/1991 | Rodak et al. | |
| 5,137,198 A | 8/1992 | Nobis et al. | |
| 5,171,249 A | 12/1992 | Stefanchik et al. | |
| 5,202,914 A | 4/1993 | Kim et al. | |
| 5,263,629 A | 11/1993 | Trumbull et al. | |
| 5,290,240 A | 3/1994 | Horres, Jr. | |

(Continued)

FOREIGN PATENT DOCUMENTS

DE 1993372 9/1968

(Continued)

OTHER PUBLICATIONS

EPO Search Report, Application No. 06255058.7, Jan. 31, 2007, pp. 1-3.

(Continued)

*Primary Examiner* — S. Thomas Hughes
*Assistant Examiner* — Sarah Simpson
(74) *Attorney, Agent, or Firm* — Dean L. Garner

(57) ABSTRACT

A surgical instrument particularly suited to endoscopic use articulates an end effector by including an articulation mechanism in an elongate shaft that incorporates an electrically actuated polymer (EAP) articulation locking mechanism actuator. Thereby, additional options for articulation become feasible, especially those that are actively powered and would otherwise dissipate heat and power if required to maintain position. Alternatively, a mechanically actuated articulation mechanism may be designed with reduced strength, and thus size, since the EAP articulation lock mechanism assists in preventing back driving after articulation. Versions of a. EAP articulation locking mechanism lock a pivoting articulation joint and others lock a flexible neck articulation joint.

6 Claims, 30 Drawing Sheets

U.S. PATENT DOCUMENTS

| | | | |
|---|---|---|---|
| 5,312,023 A | 5/1994 | Green et al. | |
| 5,330,087 A | 7/1994 | Murray et al. | |
| 5,372,124 A | 12/1994 | Takayama et al. | |
| 5,387,194 A | 2/1995 | Williams et al. | |
| 5,389,098 A | 2/1995 | Tsuruta et al. | |
| 5,397,046 A | 3/1995 | Savage et al. | |
| 5,397,324 A | 3/1995 | Carroll et al. | |
| 5,399,256 A | 3/1995 | Bohs et al. | |
| 5,403,312 A | 4/1995 | Yates et al. | |
| 5,413,267 A | 5/1995 | Solyntjes et al. | |
| 5,413,268 A | 5/1995 | Green et al. | |
| 5,431,668 A | 7/1995 | Burbank, III et al. | |
| 5,441,193 A | 8/1995 | Gravener | |
| 5,445,304 A | 8/1995 | Plyley et al. | |
| 5,465,895 A * | 11/1995 | Knodel et al. | 227/176.1 |
| 5,468,250 A | 11/1995 | Paraschac et al. | |
| 5,484,095 A | 1/1996 | Green et al. | |
| 5,503,638 A | 4/1996 | Cooper et al. | |
| 5,520,787 A | 5/1996 | Hanagan et al. | |
| 5,535,937 A | 7/1996 | Boiarski et al. | |
| 5,542,594 A | 8/1996 | McKean et al. | |
| 5,549,628 A | 8/1996 | Cooper et al. | |
| 5,555,555 A | 9/1996 | Sato et al. | |
| 5,562,239 A | 10/1996 | Boiarski et al. | |
| 5,584,425 A | 12/1996 | Savage et al. | |
| 5,599,329 A | 2/1997 | Gabbay | |
| 5,601,582 A | 2/1997 | Shelton et al. | |
| 5,609,285 A | 3/1997 | Grant | |
| 5,624,452 A | 4/1997 | Yates | |
| 5,634,584 A | 6/1997 | Okorocha et al. | |
| 5,635,721 A | 6/1997 | Bardi et al. | |
| 5,661,887 A | 9/1997 | Byrne et al. | |
| 5,665,285 A | 9/1997 | Hattori et al. | |
| 5,667,517 A | 9/1997 | Hooven | |
| 5,669,918 A | 9/1997 | Balazs | |
| 5,673,840 A | 10/1997 | Schulze et al. | |
| 5,673,841 A | 10/1997 | Schulze et al. | |
| 5,680,983 A | 10/1997 | Phyley et al. | |
| 5,688,270 A | 11/1997 | Yates et al. | |
| 5,692,668 A | 12/1997 | Schulze et al. | |
| 5,693,042 A | 12/1997 | Boiarski et al. | |
| 5,702,409 A | 12/1997 | Rayburn et al. | |
| 5,704,534 A * | 1/1998 | Huitema et al. | 227/175.1 |
| 5,709,334 A | 1/1998 | Sorrentino et al. | |
| 5,716,366 A * | 2/1998 | Yates | 606/139 |
| 5,735,445 A | 4/1998 | Vidal et al. | |
| 5,769,892 A | 6/1998 | Kingwell | |
| 5,779,130 A | 7/1998 | Alesi et al. | |
| 5,792,165 A | 8/1998 | Klieman et al. | |
| 5,797,537 A | 8/1998 | Oberlin et al. | |
| 5,810,855 A | 9/1998 | Rayburn et al. | |
| 5,826,776 A | 10/1998 | Schulze et al. | |
| 5,829,662 A | 11/1998 | Allen et al. | |
| 5,855,565 A | 1/1999 | Bar-Cohen et al. | |
| 5,865,361 A | 2/1999 | Milliman et al. | |
| 5,868,744 A | 2/1999 | Willmen | |
| 5,876,401 A | 3/1999 | Schulze et al. | |
| 5,901,895 A | 5/1999 | Heaton et al. | |
| 5,902,312 A | 5/1999 | Frater et al. | |
| 5,908,427 A | 6/1999 | McKean et al. | |
| 5,918,791 A | 7/1999 | Sorrentino et al. | |
| 5,959,852 A | 9/1999 | Deloy et al. | |
| 5,964,774 A | 10/1999 | McKean et al. | |
| 5,972,165 A | 10/1999 | Sethna et al. | |
| 6,010,054 A | 1/2000 | Johnson et al. | |
| 6,032,849 A | 3/2000 | Mastri et al. | |
| 6,033,427 A | 3/2000 | Lee | |
| 6,063,097 A | 5/2000 | Oi et al. | |
| 6,079,606 A | 6/2000 | Milliman et al. | |
| 6,109,500 A | 8/2000 | Alli et al. | |
| 6,202,914 B1 | 3/2001 | Geiste et al. | |
| 6,241,139 B1 | 6/2001 | Milliman et al. | |
| 6,302,311 B1 | 10/2001 | Adams et al. | |
| 6,330,965 B1 | 12/2001 | Milliman et al. | |
| 6,440,146 B2 | 8/2002 | Nicholas et al. | |
| 6,488,197 B1 | 12/2002 | Whitman | |
| 6,494,896 B1 | 12/2002 | D'Alessio et al. | |
| 6,503,257 B2 | 1/2003 | Grant et al. | |
| 6,503,259 B2 | 1/2003 | Huxel et al. | |
| 6,514,237 B1 * | 2/2003 | Maseda | 604/533 |
| 6,545,384 B1 | 4/2003 | Pelrine et al. | |
| 6,577,899 B2 | 6/2003 | Lebel et al. | |
| 6,583,533 B2 | 6/2003 | Pelrine et al. | |
| 6,586,859 B2 | 7/2003 | Kornbluh et al. | |
| 6,595,852 B2 | 7/2003 | Wang | |
| 6,652,521 B2 | 11/2003 | Schulze | |
| 6,656,193 B2 | 12/2003 | Grant et al. | |
| 6,667,825 B2 | 12/2003 | Lu et al. | |
| 6,669,073 B2 | 12/2003 | Milliman et al. | |
| 6,699,245 B2 | 3/2004 | Dinger et al. | |
| 6,716,233 B1 | 4/2004 | Whitman | |
| 6,740,079 B1 | 5/2004 | Eggers et al. | |
| 6,770,027 B2 | 8/2004 | Banik et al. | |
| 6,786,382 B1 | 9/2004 | Hoffman | |
| 6,830,174 B2 | 12/2004 | Hillstead et al. | |
| 6,835,173 B2 | 12/2004 | Couvillon, Jr. | |
| 6,840,246 B2 | 1/2005 | Downing | |
| 6,905,057 B2 | 6/2005 | Swayze et al. | |
| 6,913,579 B2 | 7/2005 | Truckai et al. | |
| 6,923,804 B2 | 8/2005 | Eggers et al. | |
| 6,959,852 B2 | 11/2005 | Shelton, IV et al. | |
| 6,964,363 B2 | 11/2005 | Wales et al. | |
| 6,969,395 B2 | 11/2005 | Eskuri | |
| 6,978,921 B2 | 12/2005 | Shelton, IV et al. | |
| 6,981,628 B2 | 1/2006 | Wales | |
| 6,988,649 B2 | 1/2006 | Shelton, IV et al. | |
| 7,000,819 B2 | 2/2006 | Swayze et al. | |
| 7,044,352 B2 | 5/2006 | Shelton, IV et al. | |
| 7,055,731 B2 | 6/2006 | Shelton, IV et al. | |
| 7,063,699 B2 | 6/2006 | Hess et al. | |
| 7,074,217 B2 | 7/2006 | Strul et al. | |
| 7,083,075 B2 | 8/2006 | Swayze et al. | |
| 7,111,769 B2 | 9/2006 | Wales et al. | |
| 7,140,528 B2 | 11/2006 | Shelton, IV | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,208,005 B2 | 4/2007 | Frecker et al. | |
| 7,208,421 B2 | 4/2007 | Sakamoto et al. | |
| 7,213,736 B2 | 5/2007 | Wales et al. | |
| 7,238,195 B2 | 7/2007 | Viola | |
| 7,320,700 B2 | 1/2008 | Cooper et al. | |
| 7,338,509 B2 | 3/2008 | Mattison | |
| 7,354,447 B2 | 4/2008 | Shelton et al. | |
| 7,364,061 B2 | 4/2008 | Swayze et al. | |
| 7,367,485 B2 | 5/2008 | Shelton, IV et al. | |
| 7,380,696 B2 | 6/2008 | Shelton, IV et al. | |
| 7,404,509 B2 | 7/2008 | Ortiz et al. | |
| 7,407,074 B2 | 8/2008 | Ortiz et al. | |
| 7,407,077 B2 | 8/2008 | Ortiz et al. | |
| 7,431,730 B2 | 10/2008 | Viola | |
| 7,506,790 B2 * | 3/2009 | Shelton, IV | 227/176.1 |
| 7,517,356 B2 | 4/2009 | Heinrich | |
| 7,559,452 B2 | 7/2009 | Wales et al. | |
| 7,607,557 B2 | 10/2009 | Shelton et al. | |
| 7,641,093 B2 | 1/2010 | Doll et al. | |
| 2001/0029384 A1 | 10/2001 | Nicholas et al. | |
| 2002/0068224 A1 | 6/2002 | Danda et al. | |
| 2002/0074005 A1 | 6/2002 | Hobb et al. | |
| 2002/0108112 A1 | 8/2002 | Wallace et al. | |
| 2002/0165541 A1 | 11/2002 | Whitman | |
| 2003/0065358 A1 * | 4/2003 | Frecker et al. | 606/205 |
| 2003/0069474 A1 | 4/2003 | Couvillon et al. | |
| 2003/0199870 A1 | 10/2003 | Truckai | |
| 2003/0233066 A1 * | 12/2003 | Ewers et al. | 604/27 |
| 2003/0236531 A1 | 12/2003 | Couvillon, Jr. | |
| 2004/0002726 A1 | 1/2004 | Nunez et al. | |
| 2004/0054322 A1 * | 3/2004 | Vargas | 604/95.04 |
| 2004/0097971 A1 | 5/2004 | Hughett | |
| 2004/0138700 A1 | 7/2004 | Cooper et al. | |
| 2004/0149802 A1 | 8/2004 | Whitman | |
| 2004/0232195 A1 | 11/2004 | Shelton, IV et al. | |
| 2004/0232196 A1 | 11/2004 | Shelton et al. | |
| 2004/0232197 A1 | 11/2004 | Shelton et al. | |
| 2005/0006429 A1 * | 1/2005 | Wales et al. | 227/175.1 |
| 2005/0006431 A1 | 1/2005 | Shelton, IV et al. | |
| 2005/0006434 A1 | 1/2005 | Wales et al. | |

| | | |
|---|---|---|
| 2005/0006531 A1 | 1/2005 | Tabor |
| 2005/0067457 A1 | 3/2005 | Shelton et al. |
| 2005/0067458 A1 | 3/2005 | Swayze et al. |
| 2005/0085693 A1 | 4/2005 | Belson et al. |
| 2005/0102017 A1 | 5/2005 | Mattison |
| 2005/0165415 A1 | 7/2005 | Wales |
| 2005/0173490 A1 | 8/2005 | Shelton |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0060630 A1 | 3/2006 | Shelton, IV et al. |
| 2006/0180634 A1 | 8/2006 | Shelton, IV et al. |
| 2006/0190028 A1 | 8/2006 | Wales et al. |
| 2007/0084897 A1 | 4/2007 | Shelton, IV et al. |
| 2007/0102453 A1 | 5/2007 | Morgan et al. |
| 2007/0170225 A1 | 7/2007 | Shelton, IV et al. |
| 2007/0179525 A1 | 8/2007 | Frecker et al. |
| 2007/0221701 A1 | 9/2007 | Ortiz et al. |
| 2010/0181364 A1 | 7/2010 | Shelton, IV et al. |

FOREIGN PATENT DOCUMENTS

| | | |
|---|---|---|
| DE | 4015562 | 11/1991 |
| DE | 4303544 | 9/1993 |
| DE | 19534320 | 2/1997 |
| DE | 19537299 | 4/1997 |
| DE | 19643073 | 4/1997 |
| DE | 19647354 | 5/1998 |
| EP | 0 201 883 | 11/1986 |
| EP | 0 500 353 | 8/1992 |
| EP | 0 674 876 | 10/1995 |
| EP | 0 741 996 | 11/1996 |
| EP | 0741966 | 11/1996 |
| EP | 0 832 605 | 4/1998 |
| EP | 1323384 | 7/2003 |
| EP | 1 522 264 | 4/2005 |
| EP | 1621137 | 2/2006 |
| EP | 1621141 | 2/2006 |
| EP | 1621143 | 2/2006 |
| EP | 1621151 | 2/2006 |
| EP | 1693008 | 8/2006 |
| WO | WO 99/02090 | 1/1999 |
| WO | WO 00/78222 | 12/2000 |
| WO | WO 01/56455 | 8/2001 |
| WO | WO 01/62158 | 8/2001 |
| WO | WO 01/62163 | 8/2001 |
| WO | WO 02/28268 | 4/2002 |
| WO | WO 03/088845 | 10/2003 |
| WO | WO 03/090630 | 11/2003 |
| WO | WO 03/094743 | 11/2003 |
| WO | WO 03/094746 | 11/2003 |
| WO | WO 2004/014238 | 2/2004 |
| WO | WO 2004/050971 | 6/2004 |
| WO | WO 2004/086987 | 10/2004 |

OTHER PUBLICATIONS

U.S. Appl. No. 10/441,362, filed May 20, 2003, Ho.
U.S. Appl. No. 10/441,424, filed May 20, 2003, Shelton IV et al.
U.S. Appl. No. 10/615,971, filed Jul. 9, 2003, Wales et al.
U.S. Appl. No. 10/673,929, filed Sep. 29, 2003, Shelton IV et al.
U.S. Appl. No. 11/052,387, filed Feb. 7, 2005, Shelton IV et al.
U.S. Appl. No. 11/052,632, filed Feb. 7, 2005, Rao et al.
U.S. Appl. No. 11/066,371, filed Feb. 25, 2005, Shelton IV.
U.S. Appl. No. 11/082,495, filed Mar. 17, 2005, Shelton IV.
U.S. Appl. No. 11/083,740, filed Mar. 18, 2005, Wales et al.
U.S. Appl. No. 11/162,984, filed Sep. 3, 2005, Ortiz et al.
U.S. Appl. No. 11/162,985, filed Sep. 30, 2005, Ortiz et al.
U.S. Appl. No. 11/162,986, filed Sep. 30, 2005, Ortiz et al.
U.S. Appl. No. 11/162,988, filed Sep. 30, 2005, Ortiz et al.
U.S. Appl. No. 11/162,989, filed Sep. 30, 2005, Ortiz et al.
U.S. Appl. No. 11/162,990, filed Sep. 30, 2005, Ortiz et al.
U.S. Appl. No. 11/162,991, filed Sep. 30, 2005, Ortiz et al.
U.S. Appl. No. 11/162,992, filed Sep. 30, 2005, Ortiz et al.
U.S. Appl. No. 11/240,836, filed Sep. 30, 2005, Shelton IV et al.
U.S. Appl. No. 60/591,694, filed Jul. 28, 2004, Shelton IV.
Non-Final Rejection, dated Nov. 13, 2006 for U.S. Appl. No. 11/181,046.
Non-Final Rejection dated Mar. 22, 2007 for U.S. Appl. No. 11/082,495.
Non-Final Rejection dated Aug. 7, 2007 for U.S. Appl. No. 11/162,990.
Non-Final Rejection dated Aug. 29, 2007 for U.S. Appl. No. 11/181,046.
Non-Final Rejection dated Sep. 21, 2007 for U.S. Appl. No. 11/162,986.
Non-Final Rejection dated Sep. 21, 2007 for U.S. Appl. No. 11/162,988.
Notice of Allowance dated May 23, 2006 for U.S. Appl. No. 11/096,158.
Notice of Allowance dated Jul. 25, 2006 for U.S. Appl. No. 11/066,371.
Notice of Allowance dated Aug. 14, 2006 for U.S. Appl. No. 11/157,767.
Notice of Allowance dated Aug. 22, 2006 for U.S. Appl. No. 11/181,471.
Notice of Allowance dated Dec. 1, 2006 for U.S. Appl. No. 10/955,042.
Notice of Allowance dated Aug. 31, 2007 for U.S. Appl. No. 11/096,096.
Notice of Allowance dated Sep. 12, 2007 for U.S. Appl. No. 11/240,836.
Notice of Allowance dated Sep. 19, 2007 for U.S. Appl. No. 11/082,495.
Notice of Allowance dated Oct. 1, 2007 for U.S. Appl. No. 10/955,042.
Notice of Allowance dated Mar. 13, 2008 for U.S. Appl. No. 11/240,836.
Office Action dated Mar. 7, 2006 for U.S. Appl. No. 10/955,042.
Office Action dated Mar. 26, 2008 for U.S. Appl. No. 10/955,042.
EPO Search Report, Application No. 05254680.1, Jan. 12, 2006, pp. 1-5.
EPO Search Report, Application No. 05254694.2, Jan. 12, 2006, pp. 1-5.
EPO Search Report, Application No. 05254685.0, Jan. 12, 2006, pp. 1-5.
EPO Search Report, Application No. 05254695.9, Jan. 12, 2006, pp. 1-5.
EPO Search Report, Application No. 06255062.9, Nov. 23, 2006, pp. 1-3.
EPO Search Report, Application No. 06255053.8, Jan. 25, 2007, pp. 1-3.
EPO Search Report, Application No. 06255057.9, Jan. 29, 2007, pp. 1-3.
EPO Search Report, Application No. 06255064.5, Feb. 9, 2007, pp. 1-3.
EPO Search Report, Application No. 06255065.2, Feb. 15, 2007, pp. 1-3.
Guidelines for Hand and Power Tools' http://www.osha.gov/doc/outreachtraining/htmlfiles/tools.html, OSHA, May 1996, p. 3.
Final Rejection dated Oct. 18, 2006 for U.S. Appl. No. 11/096,096.
Office Action dated Mar. 22, 2007 for U.S. Appl. No. 11/082,495.
Notice of Allowance dated Sep. 25, 2006 for U.S. Appl. No. 11/083,470.
Notice of Allowance dated Jan. 5, 2007 for U.S. Appl. No. 11/096,096.
Notice of Allowance dated Mar. 25, 2008 for U.S. Appl. No. 11/096,096.
Notice of Allowance dated Apr. 10, 2008 for U.S. Appl. No. 11/082,495.
Notice of Allowance dated Apr. 10, 2008 for U.S. Appl. No. 11/162,990.
Notice of Allowance dated Apr. 18, 2008 for U.S. Appl. No. 11/162,985.
Notice of Allowance dated Apr. 18, 2008 for U.S. Appl. No. 11/162,986.

Notice of Allowance dated Apr. 18, 2008 for U.S. Appl. No. 11/162,988.
Non-Final Rejection dated May 5, 2008 for U.S. Appl. No. 11/181,046.
Notice of Allowance dated Jun. 10, 2008 for U.S. Appl. No. 11/082,495.
Notice of Allowance dated Jun. 10, 2008 for U.S. Appl. No. 11/240,836.
EPO Search Report dated Feb. 29, 2008 for Application No. 05254681.9.
EPO Search Report dated Jan. 31, 2007 for Application No. 06255058.
Abstract—DE 4015562.
Abstract—DE 4303544.
Abstract—DE 19534320.
Abstract—DE 19537299.
Abstract—DE 19643073.
Abstract—DE 19647354.

* cited by examiner

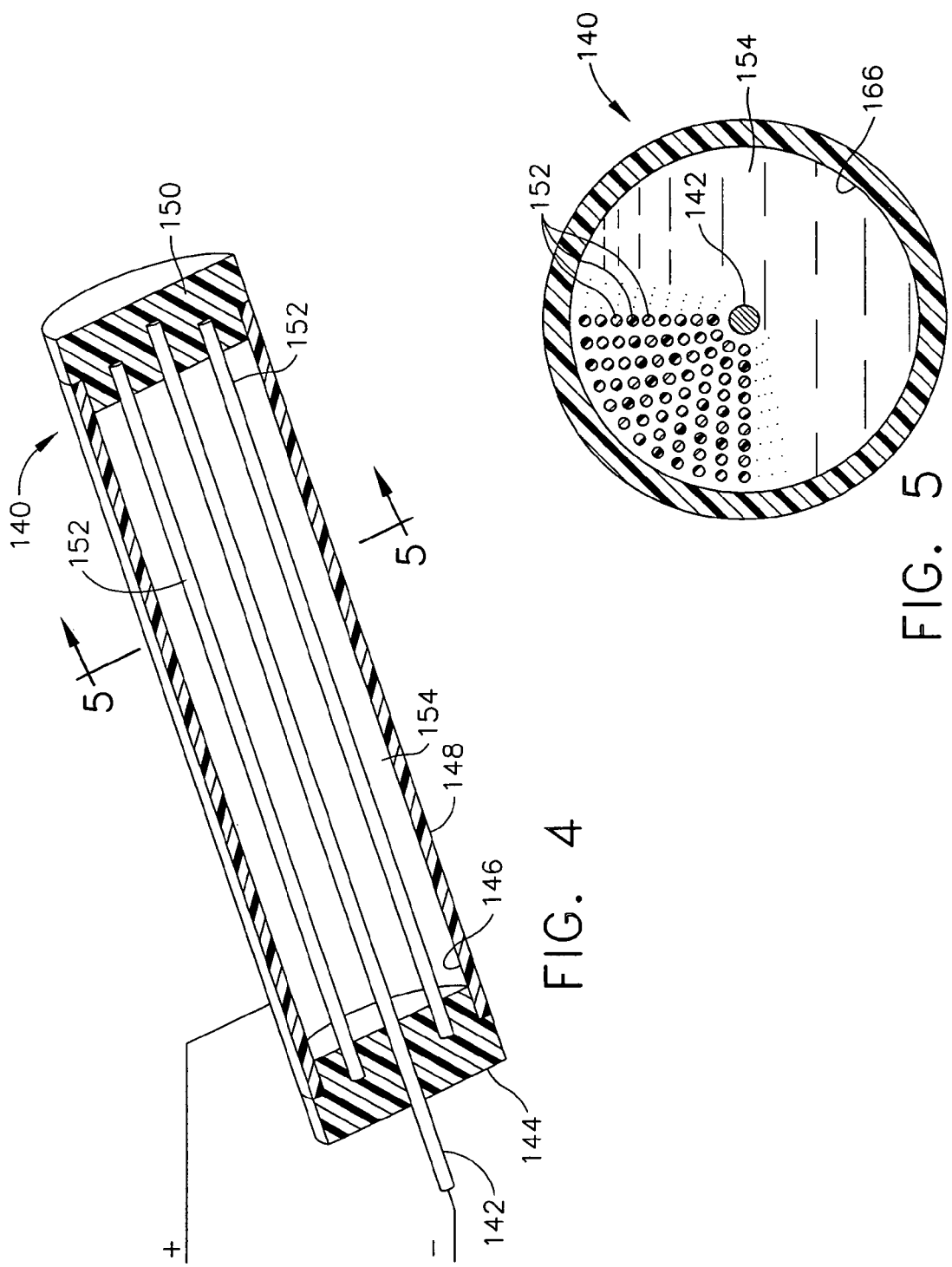

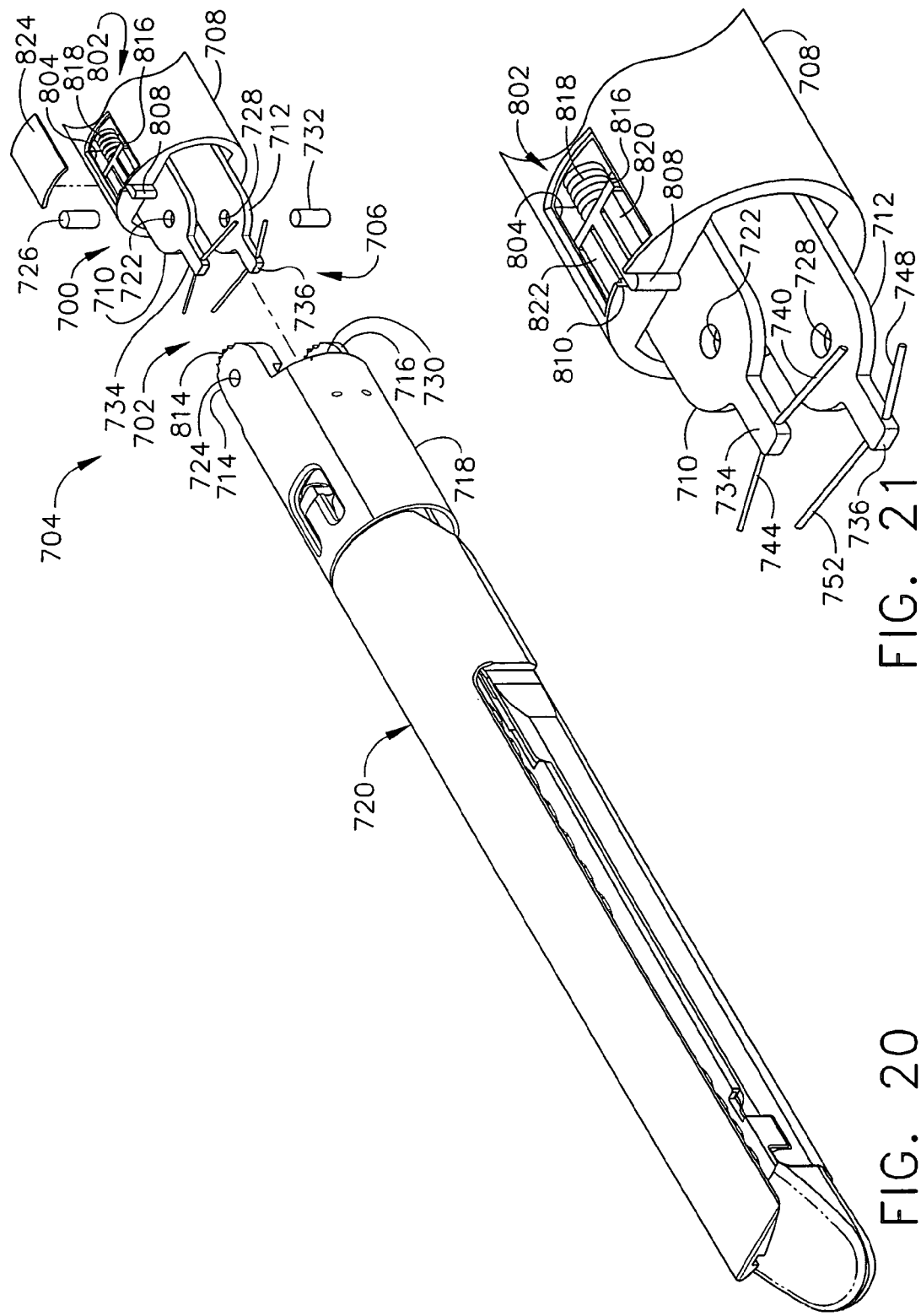

SURGICAL INSTRUMENT INCORPORATING AN ELECTRICALLY ACTUATED ARTICULATION LOCKING MECHANISM

CROSS REFERENCE TO RELATED APPLICATIONS

This application claims the benefit of U.S. provisional application Ser. No. 60/591,694, entitled "SURGICAL INSTRUMENT INCORPORATING AN ELECTRICALLY ACTUATED ARTICULATION MECHANISM" to Shelton IV, filed 28 Jul. 2004.

FIELD OF THE INVENTION

The present invention relates in general to surgical instruments that are suitable for endoscopically inserting an end effector (e.g., endocutter, grasper, cutter, staplers, clip applier, access device, drug/gene therapy delivery device, and an energy device using ultrasound, RF, laser, etc.) to a surgical site, and more particularly to such surgical instruments with an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. Pat. Ser. No. 10/443,617, "SURGICAL STAPLING INSTRUMENT INCORPORATING AN E-BEAM FIRING MECHANISM" to Shelton IV et al., filed on 20 May 2003, which is hereby incorporated by reference in its entirety, describes an improved "E-beam" firing bar for severing tissue and actuating staples. Some of the additional advantages include affirmatively spacing the jaws of the end effector, or more specifically a staple applying assembly, even if slightly too much or too little tissue is clamped for optimal staple formation. Moreover, the E-beam firing bar engages the end effector and staple cartridge in a way that enables several beneficial lockouts to be incorporated.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally referred to as "articulation". This is typically accomplished by a pivot (or articulation) joint being placed in the extended shaft just proximal to the staple applying assembly. This allows the surgeon to articulate the staple applying assembly remotely to either side for better surgical placement of the staple lines and easier tissue manipulation and orientation. This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation.

In co-pending and commonly owned U.S. patent application Ser. No. 10/615,973 "SURGICAL INSTRUMENT INCORPORATING AN ARTICULATION MECHANISM HAVING ROTATION ABOUT THE LONGITUDINAL AXIS" to Kenneth Wales et al, the disclosure of which is hereby incorporated by reference in its entirety, a rotational motion is used to transfer articulation motion as an alternative to a longitudinal motion.

While these mechanically communicated articulation motions have successfully enabled an endoscopic surgical stapling and severing instrument to articulate, development trends pose numerous challenges and barriers to entry into the market. Conflicting design objects include a shaft of as small a diameter as possible to reduce the size of the surgical opening, yet with sufficient strength to perform the several motions (e.g., closing, firing, articulation, rotation, etc.). However, these generally known articulation mechanisms have to remain robust enough to withstand being back driven by loads on the end effector.

Consequently, a significant need exists for an articulating surgical instrument that incorporates an articulation mechanism that reduces the required diameter of actuation components passing through the shaft of the instrument, yet robustly remains at the selected articulation angle thereafter.

BRIEF SUMMARY OF THE INVENTION

The invention overcomes the above-noted and other deficiencies of the prior art by providing a surgical instrument having an articulating shaft attached between a handle and an end effector. An electroactive polymer (EAP) actuator disengages an articulation lock during articulation and then reengages. Thereby, even a relatively weak articulation actuation mechanism may be employed with the articulation joint being locked thereafter, eliminating the need for the articulation actuation mechanism to be strong enough after actuation to prevent being backdriven. Thereby a shaft of advantageously small diameter may be achieved, yet have the functionality of remotely controllable actuation.

In one aspect of the invention, a surgical instrument includes a pivoting articulating joint attached between an end effector and a distal end of an elongate shaft. A locking member attached to one side of the pivoting articulating joint is resiliently urged toward locking engagement with the other side of the joint even when articulated. An electrical unlocking actuator opposes the locking member to cause disengagement so that a change in the articulation angle may be made. Then the locking member is allowed to reengage, preventing backdriving.

In another aspect of the invention, a surgical instrument includes a flexible articulation joint having vertical rows of left and right ribs allowing lateral bending to either side. Locking strips are positioned within recesses in the ribs such that when the flexible articulation joint is articulated to one side, the longitudinal length of the locking strip may be changed to force blocking features thereon to be inserted between the ribs, maintaining them in their spaced condition.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 is a perspective view of a cutaway along a longitudinal axis of a contracting EAP fiber actuator.

FIG. 5 is a front view in elevation taken in cross section along lines 5-5 of the contracting EAP fiber actuator of FIG. 4.

FIG. 20 is a right front perspective view of a partially exploded single pivot articulation joint that advantageously includes an EAP articulation locking mechanism that is biased to be normally locked.

FIG. 21 is a right front perspective view in detail of a proximal portion of the EAP articulation locking mechanism in a proximal frame ground of the single pivot articulation joint.

DETAILED DESCRIPTION OF THE INVENTION

Overview Of Articulating Shaft.

Figure 1:
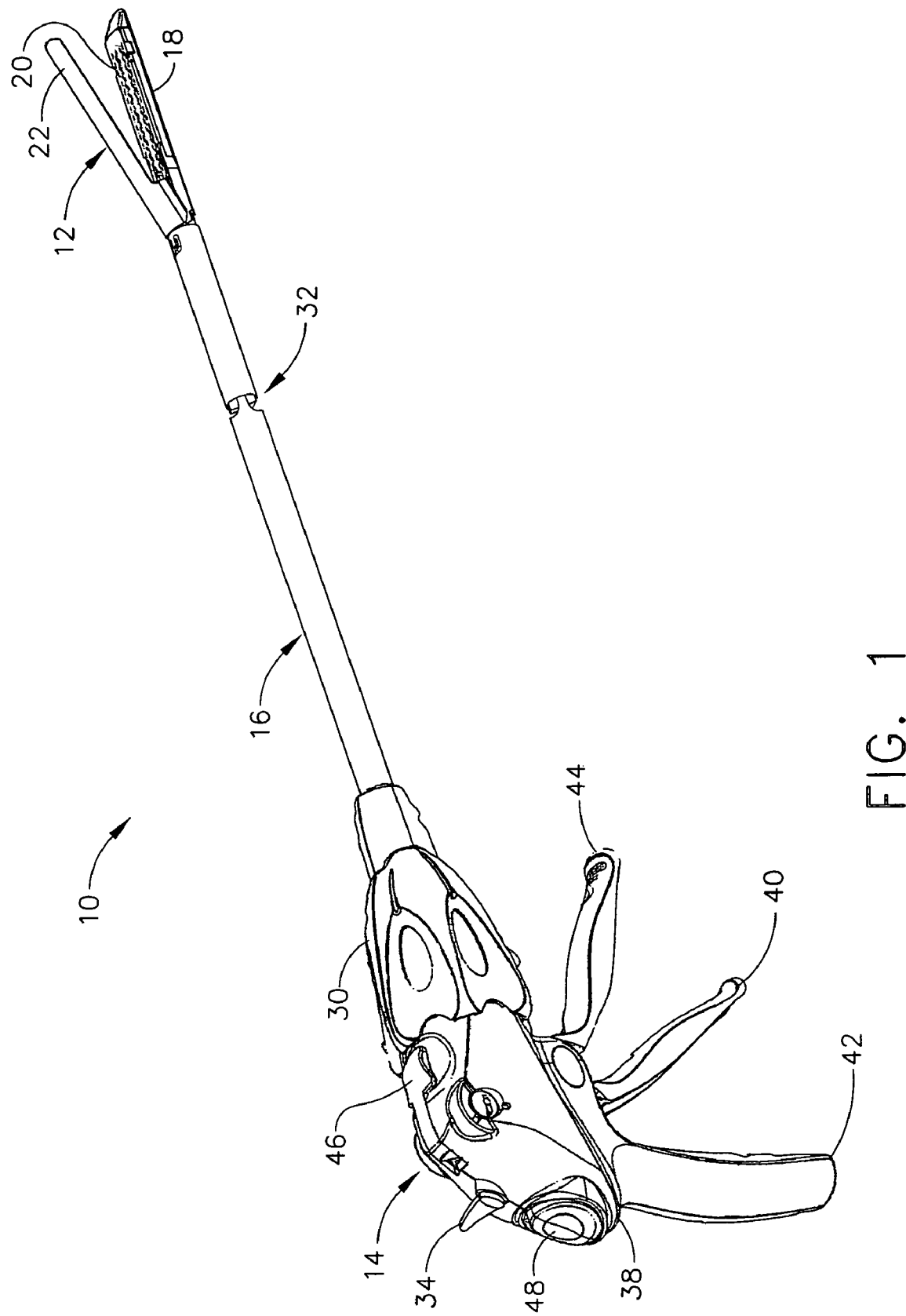
FIG. 1 is a rear perspective view of an endoscopic surgical stapling instrument for surgical stapling and severing in an open, unarticulated state.

In FIG. 1, a surgical instrument, depicted as a surgical severing and stapling instrument 10, has at its distal end an end effector of a staple applying assembly 12, spaced apart from a handle 14 by an elongate shaft 16. The staple applying assembly 12 includes a staple channel 18 for receiving a replaceable staple cartridge 20. Pivotally attached to the staple channel 18 is an anvil 22 that clamps tissue against the staple cartridge 20 for stapling and severing. When the staple applying assembly 12 is closed, its cross sectional area, as well as the elongate shaft 16 are suitable for insertion through a small surgical opening, such as through a cannula of a trocar (not shown).

Correct placement and orientation of the staple applying assembly 12 is facilitated by controls on the handle 14. In particular, a rotation knob 30 causes rotation of the shaft 16 about its longitudinal axis, and hence rotation of the staple applying assembly 12. Additional positioning is enabled at an articulation joint 32 in the shaft 16 that pivots the staple applying assembly 12 in an arc from the longitudinal axis of the shaft 16, thereby allowing placement behind an organ or allowing other instruments such as an endoscope (not shown) to be oriented behind the staple applying assembly 12. This articulation is advantageously effected by an articulation control switch 34 on the handle 14 that transmits an electrical signal to the articulation joint 32 to an Electroactive Polymer (EAP) actuator 36, powered by an EAP controller and power supply 38 contained within the handle 14. In particular, the electrical signal disengages an articulation lock by activating an EAP lock actuator (not shown in FIG. 1) during articulation.

Once positioned with tissue in the staple applying assembly 12, a surgeon closes the anvil 22 by drawing a closure trigger 40 proximally toward a pistol grip 42. Once clamped thus, the surgeon may grasp a more distally presented firing trigger 44, drawing it back to effect firing of the staple applying assembly 12, which in some applications is achieved in one single firing stroke and in other applications by multiple firing strokes. Firing accomplishes simultaneous stapling of at least two rows of staples while severing the tissue therebetween.

Retraction of the firing components may be automatically initiated upon full travel. Alternatively, a retraction lever 46 may be drawn aft to effect retraction. With the firing components retracted, the staple applying assembly 12 may be unclamped and opened by the surgeon slightly drawing the closure trigger 40 aft toward the pistol grip 42 and depressing a closure release button 48 and then releasing the closure trigger 40, thereby releasing the two stapled ends of severed tissue from the staple applying assembly 12.

It should be appreciated that herein spatial terms such as vertical, horizontal, etc. are given with reference to the figures assuming that the longitudinal axis of the surgical instrument 10 is horizontal with the anvil 22 of the staple applying assembly 12 aligned vertically on top and the triggers 40, 44 aligned vertically on the bottom of the handle 14. However, in actual practice the surgical instrument 10 may be oriented at various angles and as such these spatial terms are used relative to the surgical instrument 10 itself. Further, proximal is used to denote a perspective of a clinician who is behind the handle 14 who places the end effector 12 distal, away from himself. Handle.

In FIG. 1, the staple applying assembly 12 accomplishes the functions of clamping onto tissue, driving staples and severing tissue by two distinct motions transferred longitudinally down the shaft 16 over a shaft frame (not shown in FIG. 1 but described below regarding FIG. 7). This shaft frame assembly is proximally attached to the handle 14 and coupled for rotation with the rotation knob 30. An illustrative multi-stroke handle 14 for the surgical stapling and severing instrument 10 of FIG. 1 is described in greater detail in the co-pending and co-owned U.S. patent applications entitled "SURGICAL STAPLING INSTRUMENT INCORPORATING A MULTISTROKE FIRING POSITION INDICATOR AND RETRACTION MECHANISM" to Swayze and Shelton, Ser. No. 10/674,026, and entitled "SURGICAL STAPLING INSTRUMENT INCORPORATING A MULTI-STROKE FIRING MECHANISM WITH AUTOMATIC END OF FIRING TRAVEL RETRACTION", Ser. No. 11/052,632, filed on Feb. 7, 2005 to Kevin Doll, Jeffrey S. Swayze, Frederick E. Shelton IV, Douglas Hoffman, and Michael Setser, the disclosures of which are hereby incorporated by reference in their entirety, with additional features and variations as described herein.

While a multi-stroke handle 14 advantageously supports applications with high firing forces over a long distance, applications consistent with the present invention may incorporate a single firing stroke, such as described in co-pending and commonly owned U.S. patent application "SURGICAL STAPLING INSTRUMENT HAVING SEPARATE DISTINCT CLOSING AND FIRING SYSTEMS" to Frederick E. Shelton IV, Michael E. Setser, and Brian J. Hemmelgarn, Ser. No. 10/441,632, the disclosure of which is hereby incorporated by reference in its entirety.

Electroactive Polymers.

Electroactive polymers (EAPs) are a set of conductive doped polymers that change shape when an electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from 1V to 4 kV depending on the polymer and ionic fluid used. Some of the EAPs contract when voltage is applied and some expand. The EAPs may be paired to mechanical means such as springs or flexible plates to change the effect that is caused when the voltage is applied.

There are two basic types of electroactive polymers and multiple configurations of each type. The two basic types are a fiber bundle and a laminate version. The fiber bundle consists of fibers around 30-50 microns. These fibers may be woven into a bundle much like textiles and are often called EAP yarn because of this. This type of EAP contracts when voltage is applied. The electrodes are usually a central wire core and a conductive outer sheath, which also serves to contain the ionic fluid that surrounds the fiber bundles. An example of a commercially available fiber EAP material is manufactured by Santa Fe Science and Technology and sold as PANION™ fiber and is described in U.S. Pat. No. 6,667, 825, which is hereby incorporated by reference in its entirety.

The other type is a laminate structure, which consists of a layer of EAP polymer, a layer of ionic gel and two flexible plates that are attached to either side of the laminate. When a voltage is applied the square laminate plate expands in one direction and contracts in the perpendicular direction. An example of a commercially available laminate (plate) EAP material is from Artificial Muscle Inc, a division of SRI Laboratories. Plate EAP material is also available from EAMEX of Japan and is referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. It may also be adhered to either side of a flexible plate. When one side of the flexible plate EAP is energized, it expands flexing the plate in the opposite direction. This allows the plate to be flexed either direction depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration, when the electrical field is applied to the electrodes, the strands of EAP shorten. This configuration of EAP actuator is called a fiber EAP actuator. Likewise, the laminate configuration may be placed in numerous layers on either side of a flexible plate or merely in layers on itself to increase its capabilities. Typical fiber structures have an effective strain of 2-4% where the typical laminate version achieves 20-30% utilizing much higher voltages.

Figure 2:
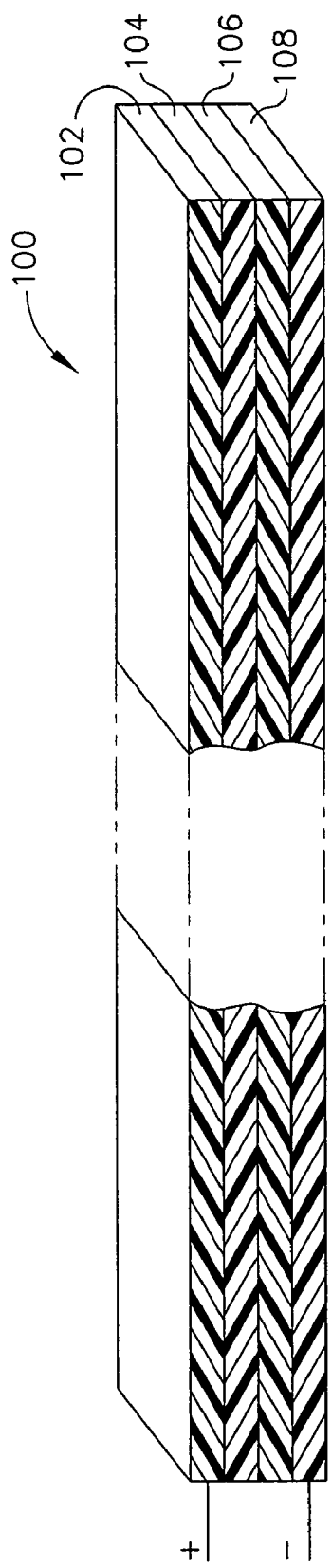
FIG. 2 is a perspective view of a laminate Electroactive Polymer (EAP) composite.
Figure 3:
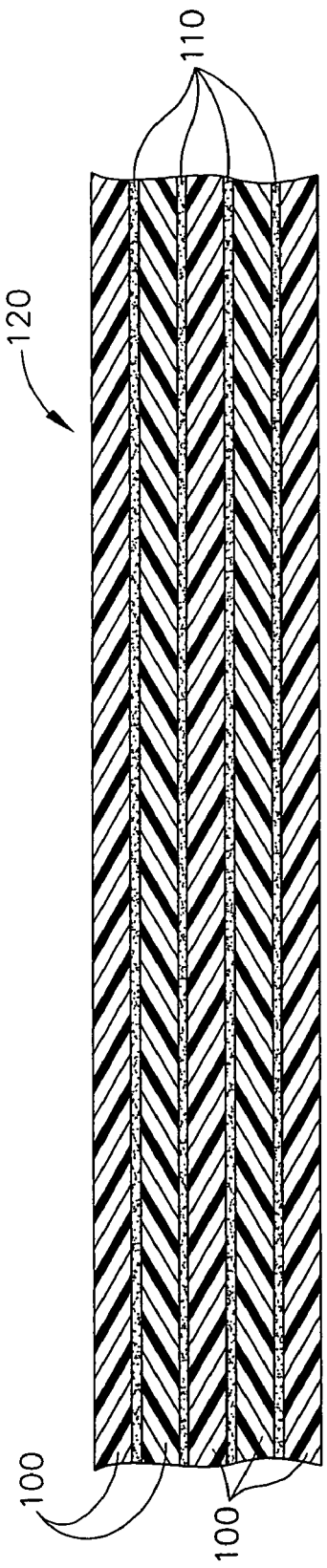
FIG. 3 is a perspective view of an EAP plate actuator formed from a stack formed from an adhesively affixed plurality of laminate EAP composites of FIG. 2.

In FIG. 2, a laminate EAP composite 100 is depicted being formed from a positive plate electrode layer 102 attached to an EAP layer 104, which in turn is attached to an ionic cell layer 106, which in turn is attached to a negative plate electrode layer 108. In FIG. 3, a plurality of five laminate EAP composites 100 are affixed in a stack by adhesive layers 110 therebetween to form an EAP plate actuator 120. It should be appreciated that opposing EAP actuators 120 may be formed that can selectively bend in either direction.

In FIGS. 4-5, a contracting EAP fiber actuator 140 includes a longitudinal platinum cathode wire 142 that passes through an insulative polymer proximal end cap 144 through an elongate cylindrical cavity 146 formed within a plastic cylinder wall 148 that is conductively doped to serve as a positive anode. A distal end of the platinum cathode wire 142 is embedded into an insulative polymer distal end cap 150. A plurality of contracting polymer fibers 152 are arranged parallel with and surrounding the cathode wire 142 and have their ends embedded into respective end caps 144, 150. The plastic cylinder wall 148 is peripherally attached around respective end caps 144, 150 to enclose the cylindrical cavity 146 to seal in ionic fluid or gel 154 that fills the space between contracting polymer fibers 152 and cathode wire 142. When a voltage is applied across the plastic cylinder wall (anode) 148 and cathode wire 142, ionic fluid enters the contracting polymer fibers 152, causing their outer diameter to swell with a corresponding contraction in length, thereby drawing the end caps 144, 150 toward one another.

EAP Actuated Articulation Joint.

In FIGS. 6-13, a surgical severing and stapling instrument 200 includes an EAP actuated articulation joint 202 that is formed in its elongate shaft 204 proximate to the end effector, which is illustrated by the surgical stapling and severing assembly 12 that advantageously responds to separate closure and firing motions that are transferred longitudinally by the elongate shaft 204. The EAP actuated articulation joint 202 advantageously adds the desirable clinical flexibility of articulating the staple applying assembly 12.

Figure 6:
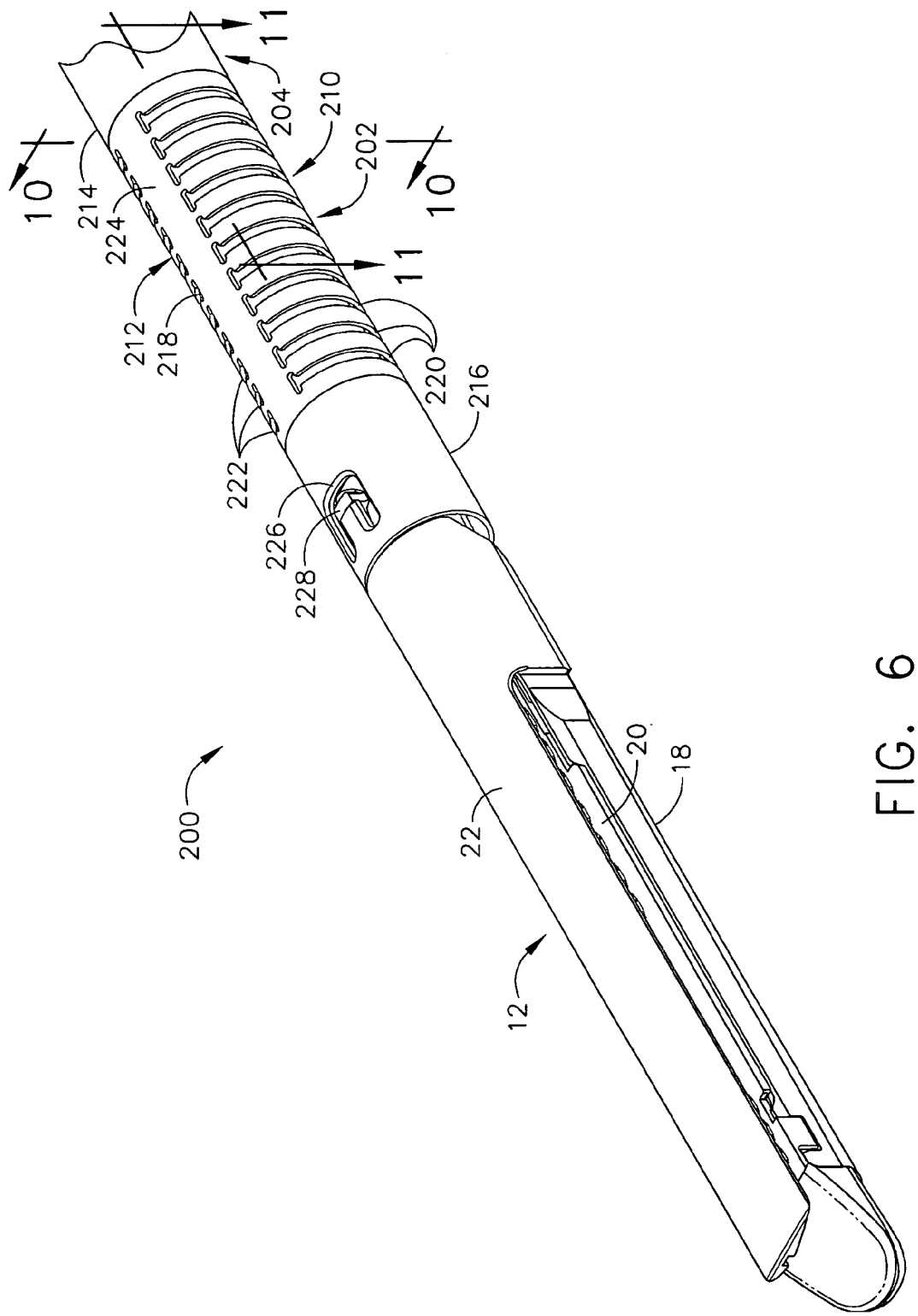
FIG. 6 is a front right perspective view of an EAP actuated articulation joint for the surgical instrument of FIG. 1 with a flex closure sleeve assembly and a pivoting frame assembly and a closed staple applying assembly.
Figure 7:
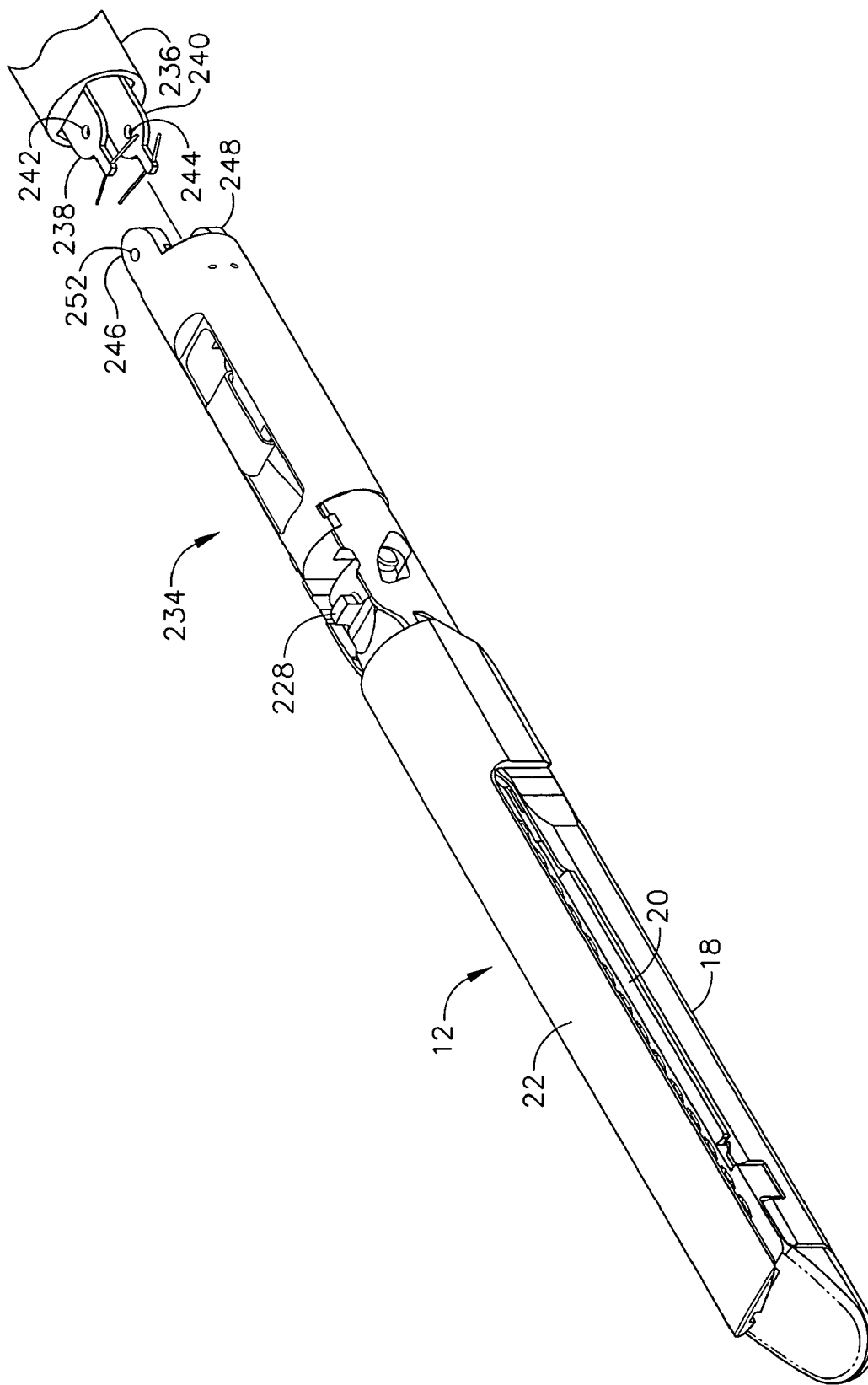
FIG. 7 is a front right perspective view of the EAP actuated articulation joint and closed staple applying assembly of FIG. 6 with a flexible closure sleeve assembly removed and a single pivot frame assembly partially exploded.
Figure 8:
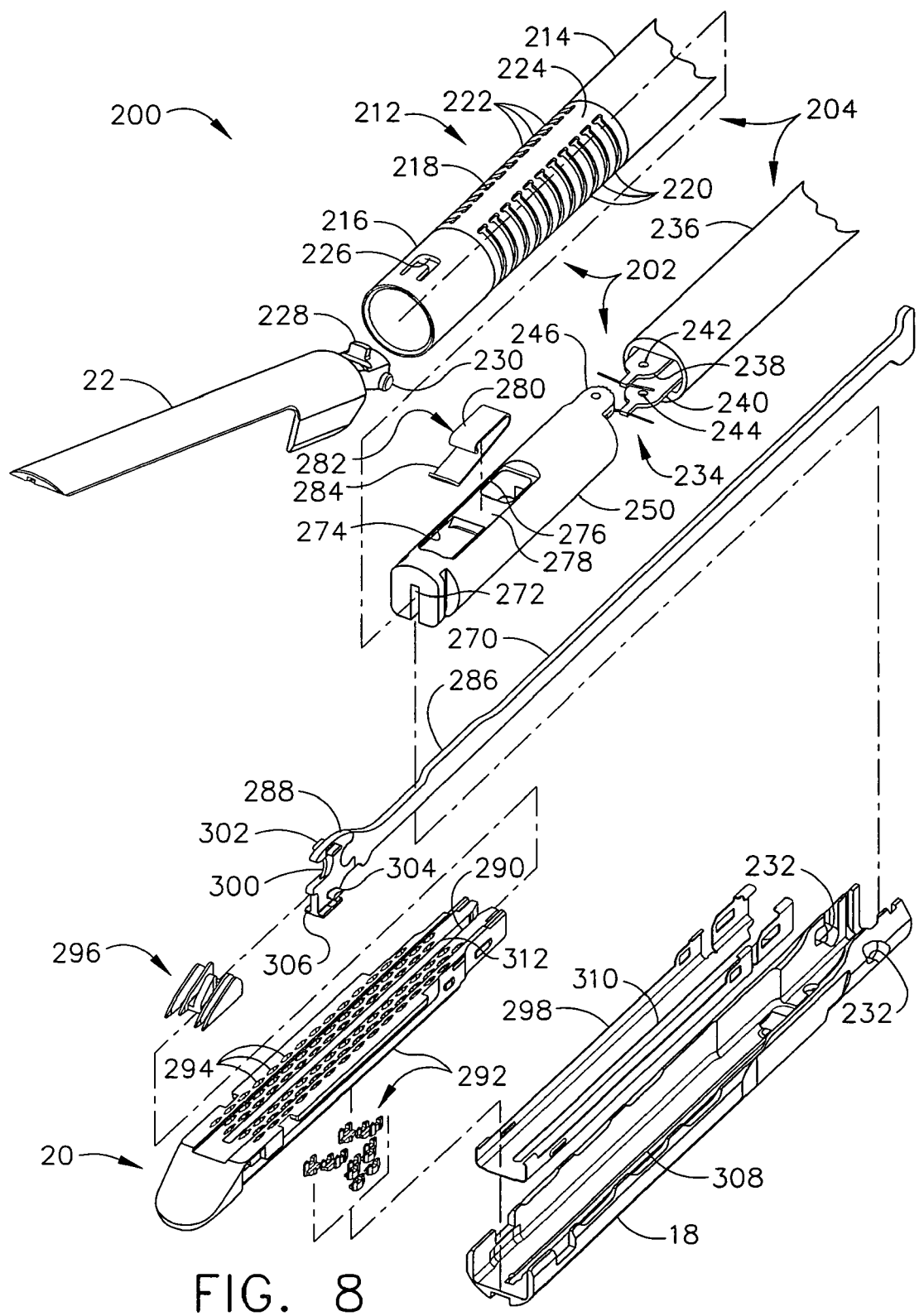
FIG. 8 is a front right exploded perspective view of the EAP actuated articulation joint and staple applying assembly of FIG. 6.

In the illustrative version of FIGS. 6-13, the EAP actuated articulation joint 202 is more particularly a flexible closure and pivoting frame articulation joint 210, which in FIG. 6 is shown to include a flexible closure sleeve assembly 212 having a proximal closure tube 214 and distal closure ring 216 connected by a flexible closure tube 218. Left and right longitudinal rows of vertical slits 220, 222 formed in the flexible closure tube 218 allow flexing to the right or to the left for articulation, yet an uninterrupted top longitudinal band 224 transfers a longitudinal closure motion regardless of the amount of such flexing. It should be appreciated that an identical uninterrupted bottom longitudinal band runs along the bottom of the flexible closure tube 218 (not shown) and is opposite to and cooperates with the top longitudinal band 224 in transferring this motion. In particular, a top portion of the distal closure ring 216 includes a horseshoe aperture 226 that engages an anvil closure feature 228 of the anvil 22. In FIG. 7, the anvil 22 includes laterally projecting pivot pins 230 at its proximal end that pivotally engage pivot apertures 232 formed near the proximal end of the elongate channel 18 (FIGS. 7-8). The slightly more distal anvil closure feature 228 thus imparts a closing motion when the flexible closure sleeve assembly 212 moves distally and imparts an opening motion when moving proximally. The flexible closure tube 218 may bend along the length of the left and right longitudinal rows of vertical slits 220, 222, thus accommodating an encompassed single pivot frame assembly 234 of the flexible closure and pivoting frame articulation joint 210 when articulated.

Figure 9:
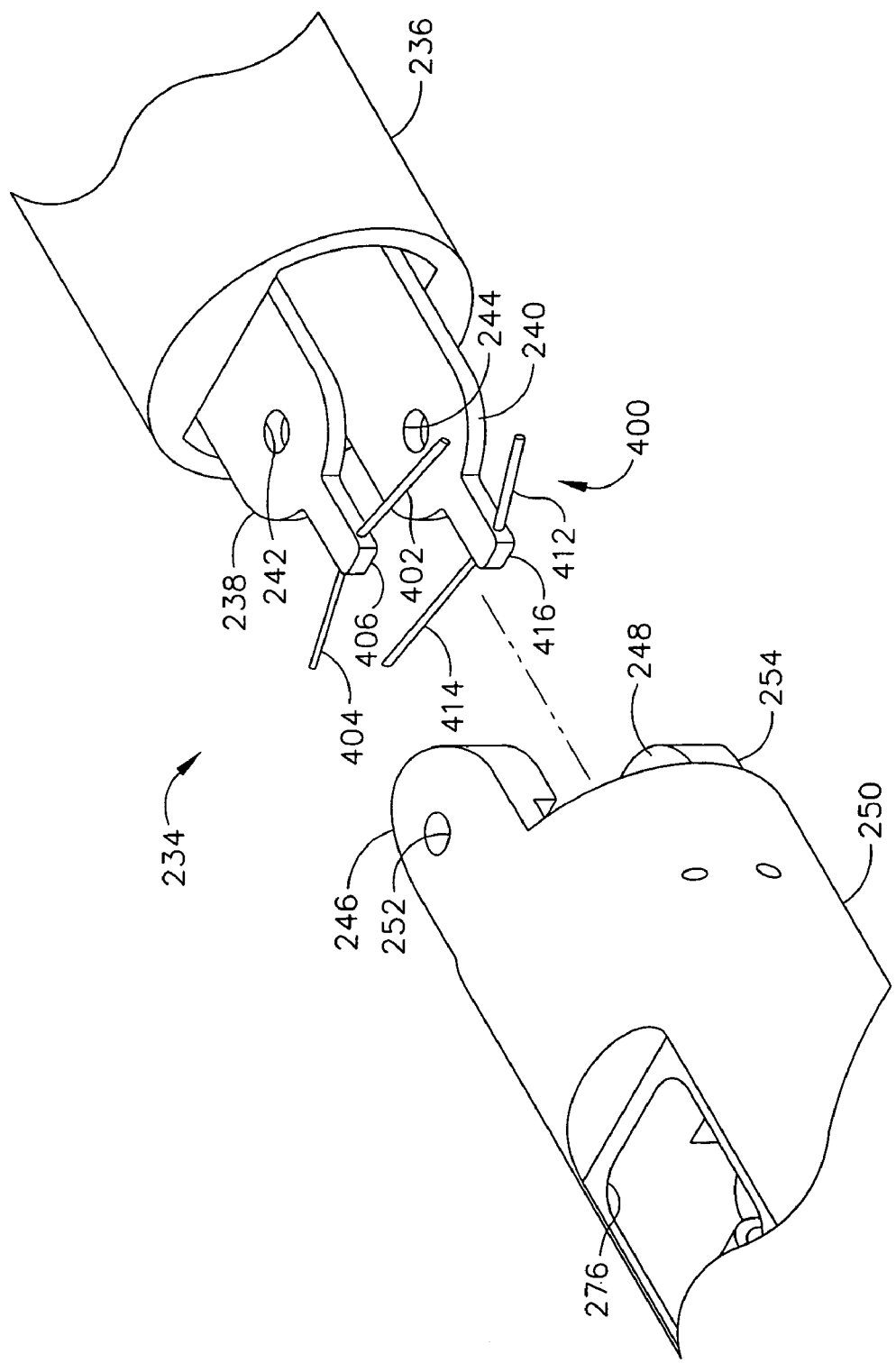
FIG. 9 is a detail view of the exploded single pivot frame assembly including EAP fiber actuators of FIG. 7.
Figure 10:
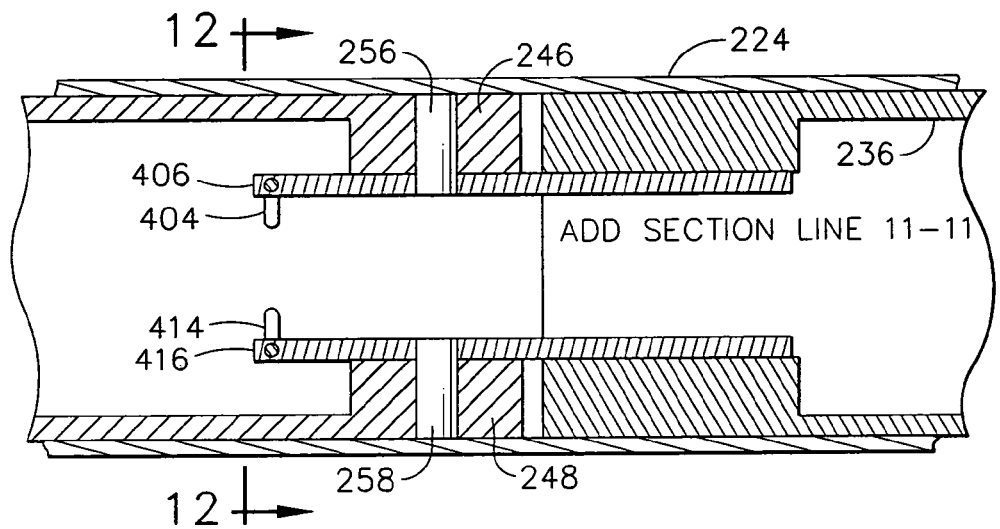
FIG. 10 is a right side view in elevation taken in cross section along lines 10-10 of FIG. 6 through a pivot axis of the EAP actuated articulation joint and looking right to see a pair of EAP fiber actuators.
Figure 11:
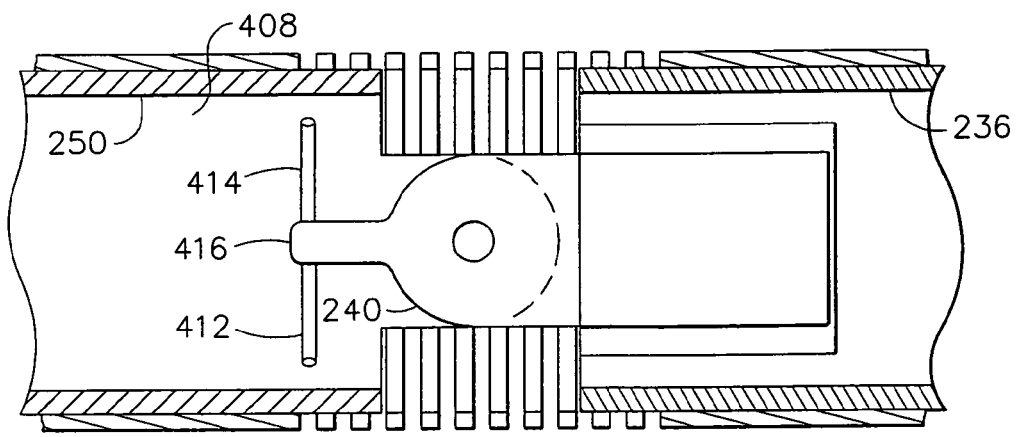
FIG. 11 is top view taken in cross section along lines 11-11 of FIG. 11 through a longitudinal axis of the EAP actuated articulation joint looking down to see a lower moment arm and lower EAP fiber actuators.
Figure 12:
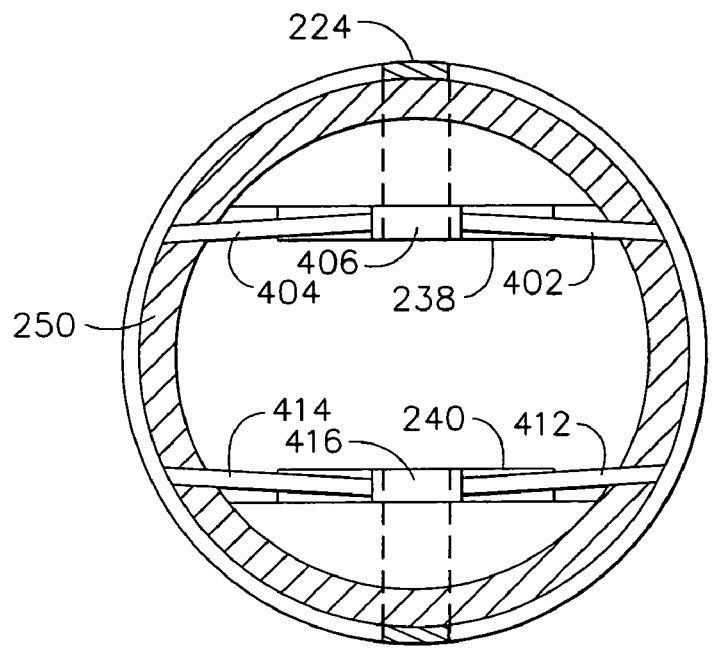
FIG. 12 is a front view in elevation taken in cross section along lines 12-12 of FIG. 10 along the lateral EAP fiber actuators.
Figure 13:
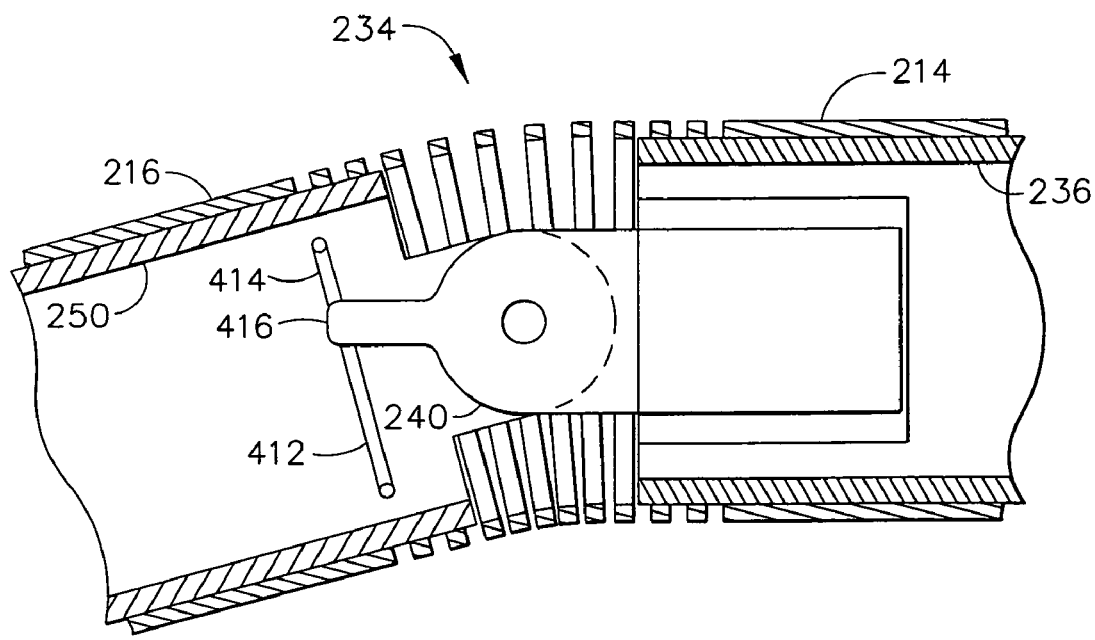
FIG. 13 is a top view of the EAP actuated articulation joint of FIG. 11 with the right upper and lower EAP fiber actuators contracted to articulate the staple applying assembly to the left.

With particular reference to FIGS. 7-9, the single pivot frame assembly 234 includes a proximal frame ground 236 with distally projecting top and bottom pivot tabs 238, 240, each having a respective top and bottom pivot pin hole 242, 244. Corresponding top and bottom pivot tangs 246, 248 project proximally from a distal frame ground 250, each tang 246, 248 with respective top and bottom pivot pin holes 252, 254 pivotally engaging the proximal frame ground 236. In particular, the vertically aligned top pivot pin holes 242, 252 and bottom pivot pin holes 244, 254 are respectively engaged by top and bottom frame pivot pins 256, 258 (FIG. 10).

In FIG. 8, an implement portion 260 of the surgical instrument 200 formed by the elongate shaft 16 and staple applying assembly 12 further includes a firing bar 270 that longitudinally translates through the proximal frame ground 218, through the flexible closure and pivoting frame articulation joint 210, and through a firing slot 272 in the distal frame ground 250 into the staple applying assembly 12. Distal and proximal square apertures 274, 276 formed on top of the distal frame ground 250 define a clip bar 278 therebetween that receives a top arm 280 of a clip spring 282 whose lower, distally extended arm 284 asserts a downward pressure on a raised portion 286 along an upper portion of the firing bar 270 corresponding to the empty/missing cartridge lockout portion of firing travel.

With particular reference to FIG. 8, a distally projecting end of the firing bar 270 is attached to an E-beam 288 that assists in spacing the anvil 22 from the staple cartridge 20, severs tissue, and actuates the staple cartridge 20. The staple cartridge 20 includes a molded cartridge body 290 that holds a plurality of staples resting upon staple drivers 292 within respective upwardly open staple apertures 294. A wedge sled 296 is driven distally by the E-beam 28 21'8, sliding upon a cartridge tray 298 that holds together the various components of the replaceable staple cartridge 20. The wedge sled 296 upwardly cams the staple drivers 292 to force out the staples into deforming contact with the anvil 22 while a cutting surface 300 of the E-beam 288 severs clamped tissue. It should be appreciated that upper pins 302 of the E-beam 288 engage the anvil 22 during firing while middle pins 304 and a bottom foot 306 engage respective top and bottom surfaces of a longitudinal slot 308 formed in the elongate channel 18, with a corresponding longitudinal opening 310 in the cartridge tray 298 and a rearwardly open vertical slot 312 in the cartridge body 290. Thereafter, the firing bar 270 is retracted proximally, retracting as well the E-beam 288, allowing the anvil 22 to be opened to release the two stapled and severed tissue portions (not shown).

The staple applying assembly 12 is described in greater detail in co-pending and commonly-owned U.S. patent application Ser. No. 10/955,042, "ARTICULATING SURGICAL STAPLING INSTRUMENT INCORPORATING A TWO-PIECE E-BEAM FIRING MECHANISM" to Frederick E. Shelton IV, et al., filed 30 Sep. 2004, the disclosure of which is hereby incorporated by reference in its entirety.

With particular reference to FIGS. 9-13, an EAP actuator system 400 advantageously actuates the single pivot frame assembly 234 in response to an electrical articulation signal (not shown) received from the handle 14. In the illustrative version of FIGS. 7-13, top left and top right EAP fiber actuators 402, 404 attach horizontally to each lateral side of a top distally projecting moment arm 406 attached to the top pivot tab 238. The outer ends of the top left and top right EAP fiber actuators 402, 404 are attached to respective upper left and right lateral attachment points 406, 408 of an inner diameter 410 of the distal frame ground 250. Similarly, bottom left and bottom right EAP fiber actuators 412, 414 attach horizontally to each lateral side of a bottom distally projecting moment arm 416 attached to the top pivot tab 238. The outer ends of the bottom left and bottom right EAP fiber actuators 412, 414 are attached to respective lower left and right lateral attachment points 418, 420 of the inner diameter 410 of the distal frame ground 250. The attachments points 406, 408, 418, 420 are shown to pass through the distal frame ground 250 in FIG. 12 with the left attachment points 406, 418 visible on the exterior of the distal frame ground 250 in FIG. 9. Activating one pair of EAP actuators, such as in FIG. 13, and in particular reference to the upper and lower right EAP fiber actuators 404, 414, causes them to contract, drawing the upper and lower moment arms 406, 416 toward the right side of the distal frame ground 250, thereby stretching the upper and lower EAP fiber actuators 402, 412, collapsing the left longitudinal row of vertical slits 220, and expanding the right longitudinal row of vertical slits 222.

Figure 14:
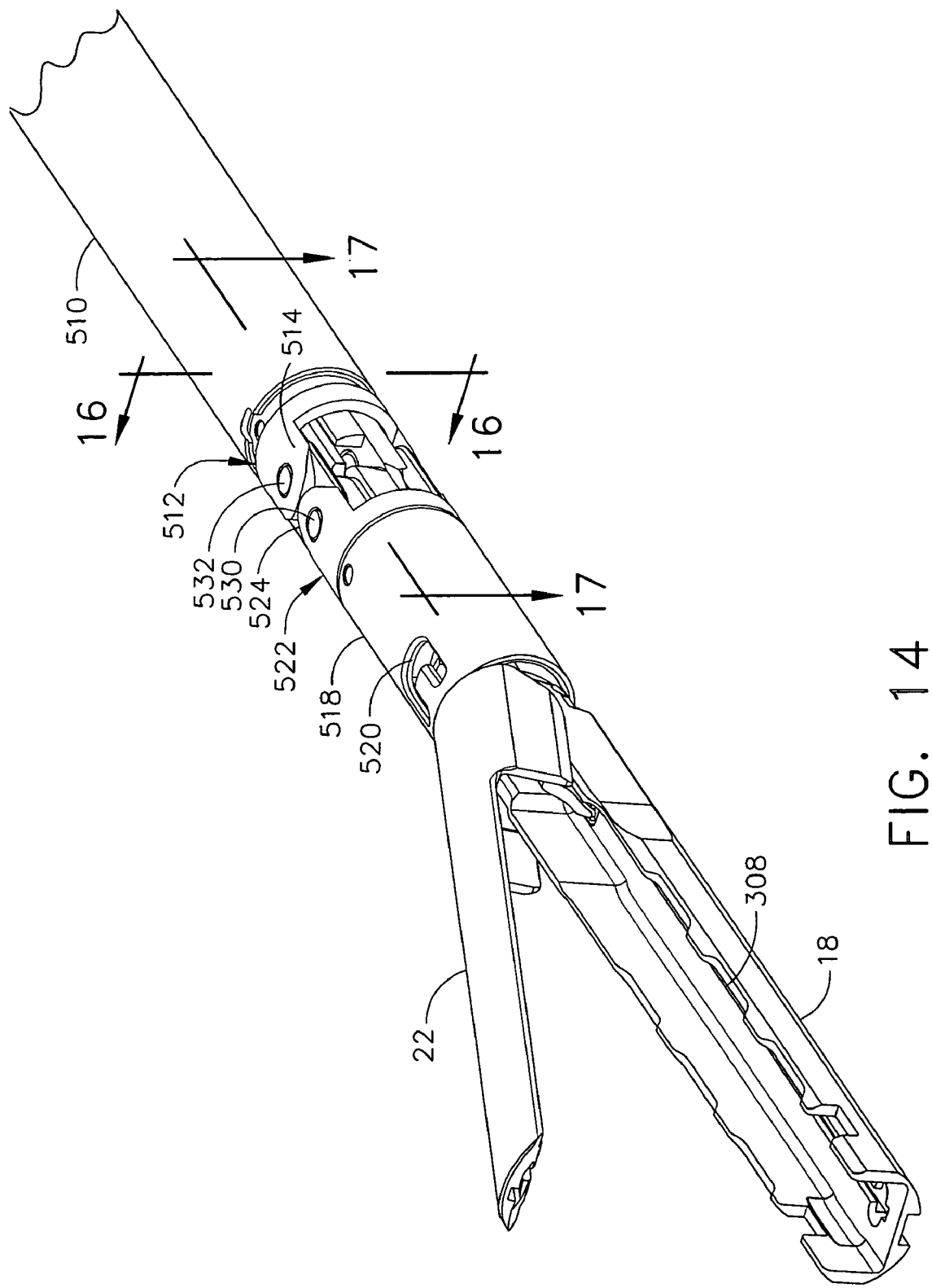
FIG. 14 is front right perspective view of an additional alternative EAP actuated articulation joint that includes a double pivot closure sleeve assembly in a proximal position opening the anvil of the end effector.

In FIGS. 14-18, a surgical severing and stapling instrument 500 includes an alternative EAP actuated articulation joint 502 that includes a double pivot closure sleeve assembly 504 (FIGS. 14-15) and a single pivot frame assembly 506 (FIGS. 15-18). In FIG. 14, the staple applying assembly 12 is depicted with the replaceable staple cartridge 20 removed and the anvil 22 open. Thus, the double pivot closure sleeve assembly 504 is at its proximal position with its distal pivoting axis aligned with a pivoting axis of the frame assembly 506. It should be appreciated that with the closure sleeve assembly 504 moved distally to close the anvil 22, a proximal pivot axis of the closure sleeve assembly 504 also pivots in order to translate over an articulated frame assembly 506.

Figure 15:
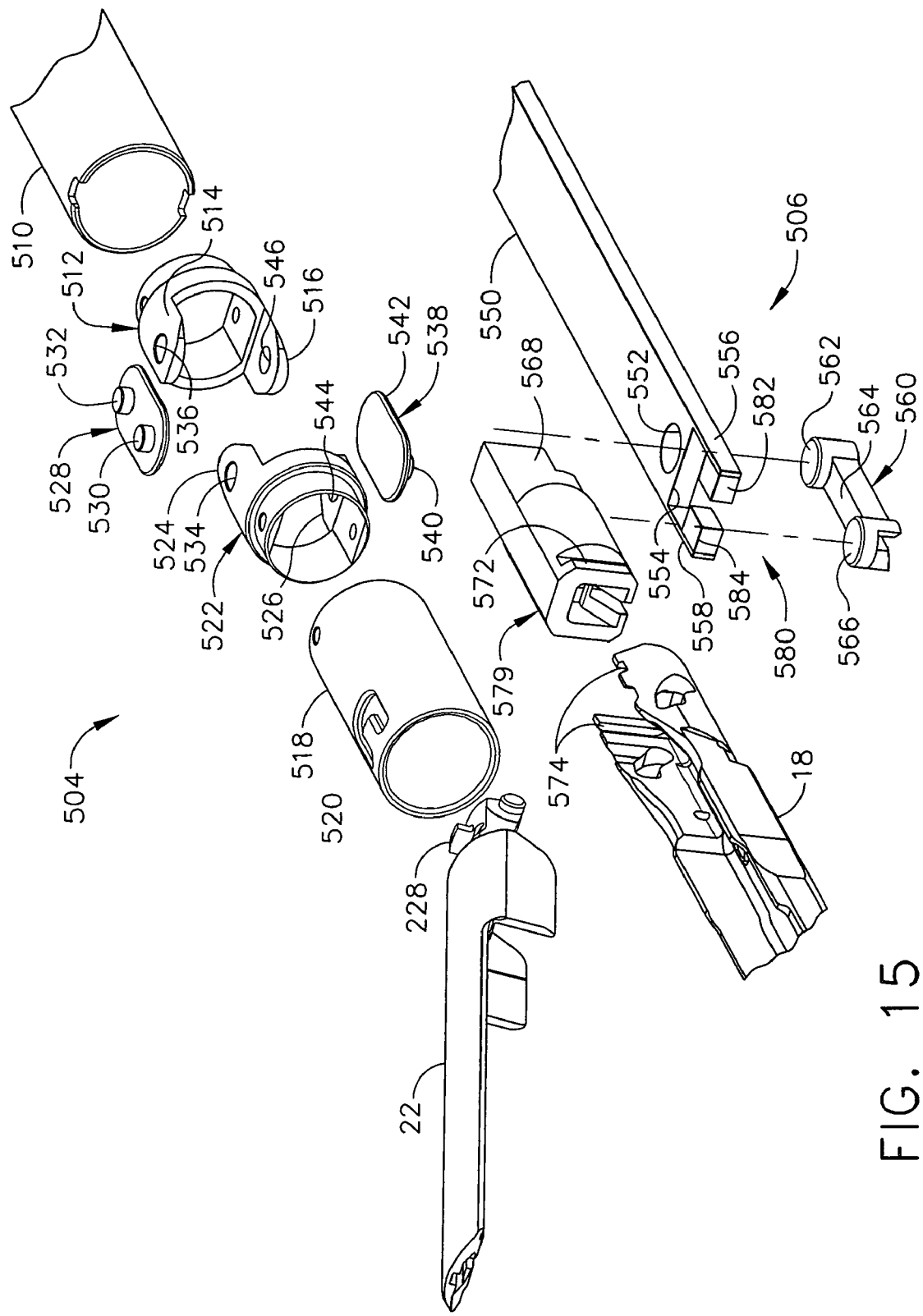
FIG. 15 is front right exploded view of the additional alternative EAP actuated articulation joint of FIG. 14 including the double pivot closure sleeve assembly and a single pivot frame assembly.
Figure 16:
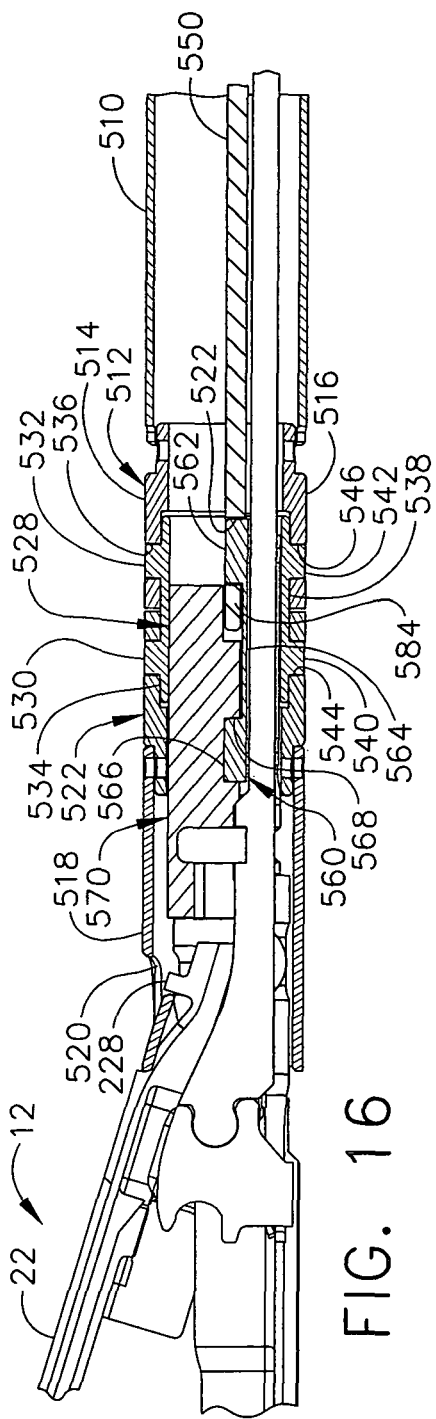
FIG. 16 is right side view in elevation of the alternative EAP actuated articulation joint taken in cross section along lines 16-16 of FIG. 14 with firing components included.
Figure 17:
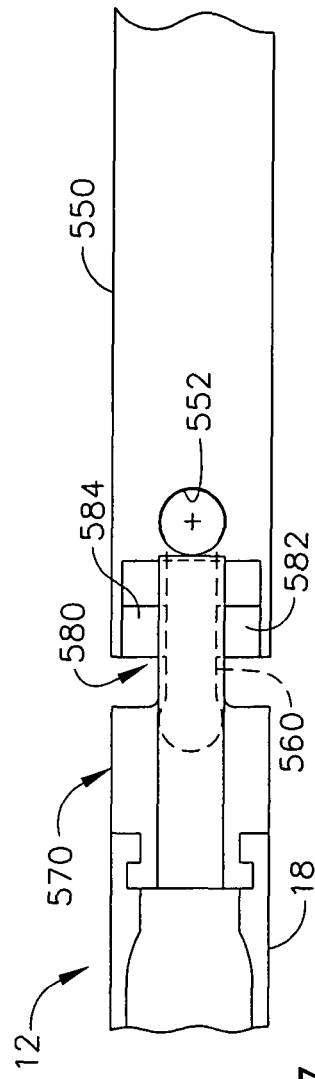
FIG. 17 is a top view of the alternative EAP actuated articulation joint in an unarticulated condition taken in cross section along lines 17-17 of FIG. 14.

With particular reference to FIG. 15, the double pivot closure sleeve assembly 504 includes a proximal closure tube 510 whose distal end is keyed to attach to a proximal closure ring 512 having upper and lower distally projecting tangs 514, 516. A distal closure tube 518, which includes a horseshoe aperture 520 to engage the anvil closure feature 228 on the anvil 22, is proximally pinned to a distal closure ring 522 having upper and lower proximally projecting tangs 524, 526. An upper double pivot link 528 includes upwardly projecting distal and proximal pivot pins 530, 532 that engage respectively an upper distal pin hole 534 in the upper proximally projecting tang 524 and an upper proximal pin hole 536 in the upper distally projecting tang 514. A lower double pivot link 538 includes downwardly projecting distal and proximal pivot pins 540, 542 that engage respectively a lower distal pin hole 544 in the lower proximally projecting tang 526 and a lower proximal pin hole 546 in the lower distally projecting tang 516.

With particular reference to FIGS. 15-18, the single pivot frame assembly 506 includes a proximal frame ground 550 whose distal end includes a pivot pin hole 552 centered and proximal to a distally open pivot recess 554 defined between left and right moment arms 556, 558. A dog bone link 560 includes a proximal pin 562 that upwardly engages the pivot pin hole 552 in the proximal frame ground 550 and a center bar 564 that pivots between the left and right moment arms 556, 558. A distal pin 566 of the dog bone link 560 is rigidly attached into a lower proximal bore 568 in a distal frame ground 570 having distal lateral guides 572 that engage proximal guides 574 in the elongate channel 18.

Figure 18:
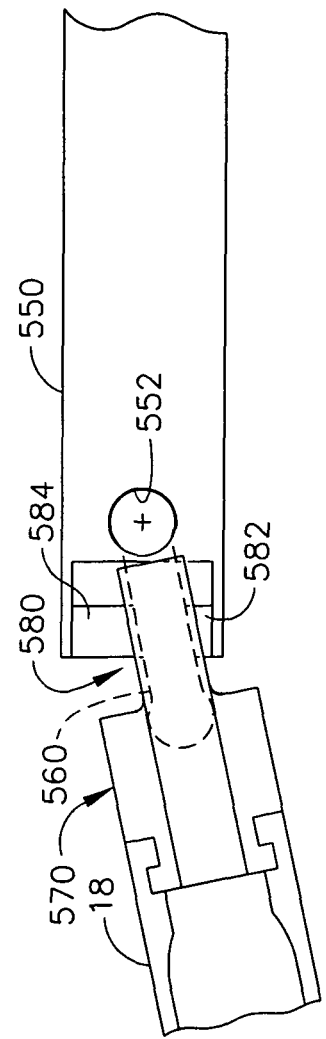
FIG. 18 is a top view of the alternative EAP actuated articulation joint in a leftward articulated condition taken in cross section along lines 17-17 of FIG. 14.

An EAP actuation system 580 includes left and right EAP stack actuators 582, 584 that selectively expand to assert an articulation force on the center bar 564 of the dog bone link 560, which passively compresses the other EAP stack actuator. In FIG. 18, the right EAP stack actuator 582 has expanded, pivoting the dog bone link 560, and thus the staple applying assembly 12, to the left and passively compressing the left EAP stack actuator 584.

Figure 19:
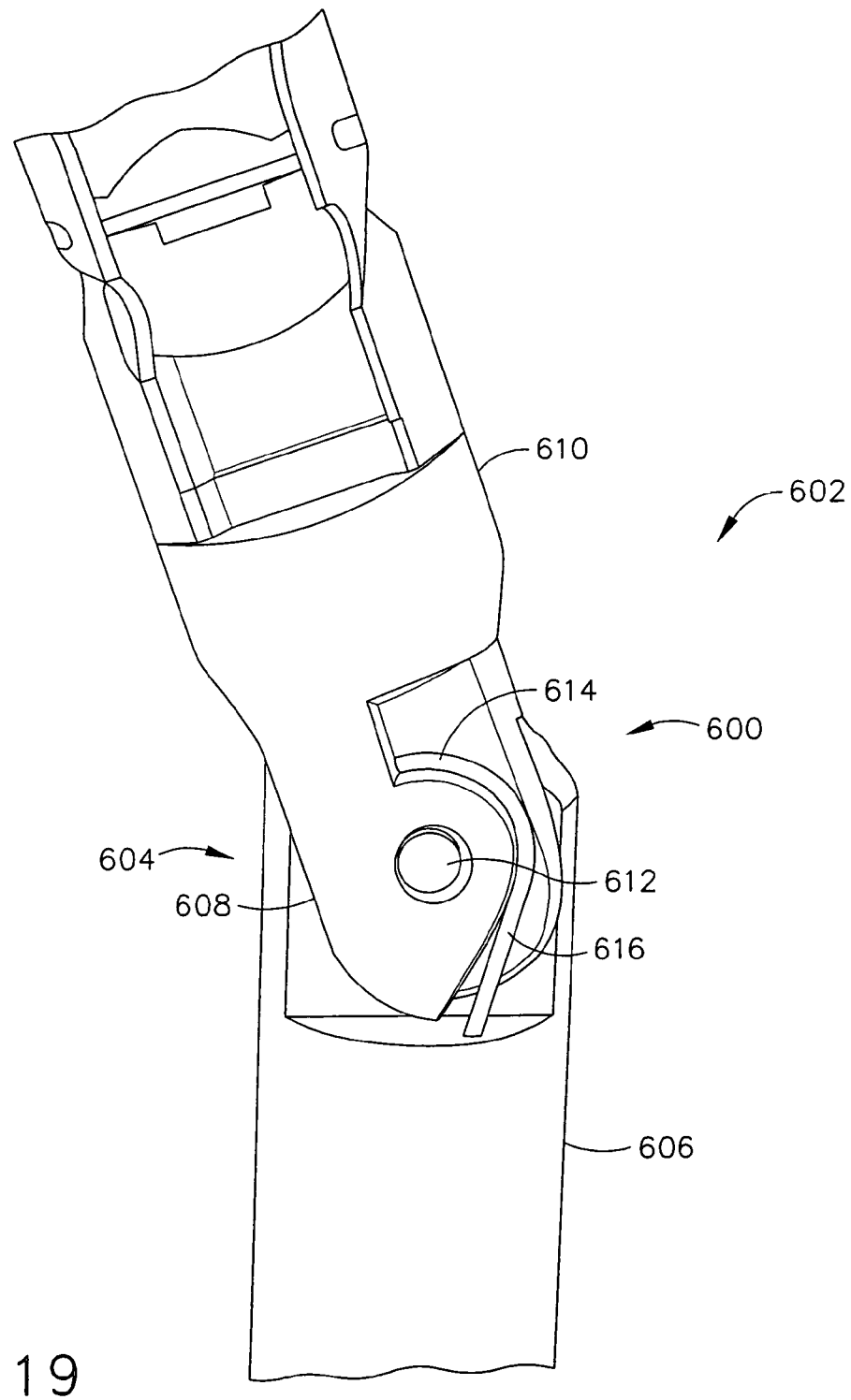
FIG. 19 is yet another alternative EAP actuated articulation joint in a slightly articulated condition with a contracting EAP fiber actuator positioned to straighten the joint.
Figure 22:
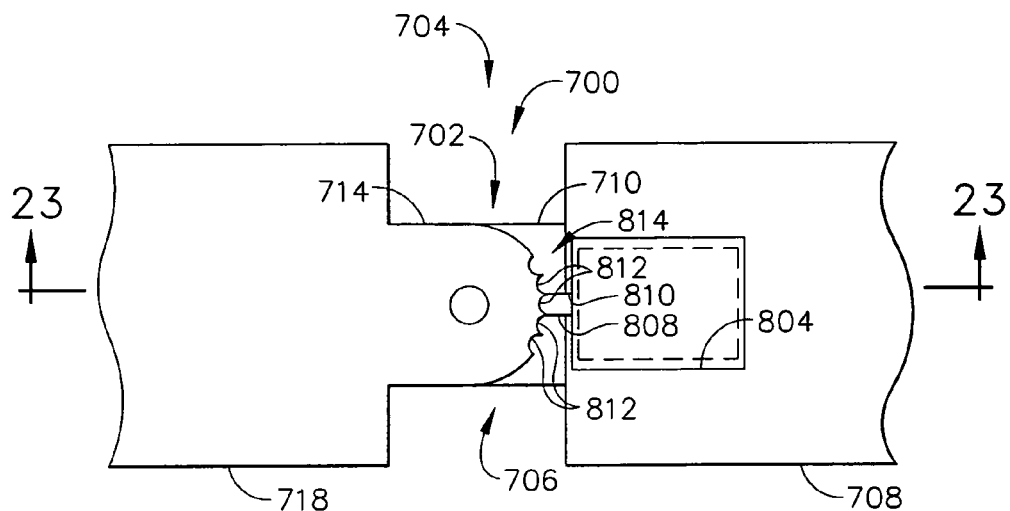
FIG. 22 is a top view of the single pivot articulation joint of FIG. 20.

In FIG. 19, yet another alternative EAP actuated articulation joint 600 for a surgical instrument 602 includes a single pivoting frame assembly 604 wherein a proximal frame ground 606 is engaged to a distally projecting tang 608 from a distal frame ground 610 at a pivot pin 612. The distally projecting tang 608 is recessed on a right lateral side to define a half teardrop shaped pulley 614 on the right side of the pivot pin 612. Attached to a distal point of the half teardrop shaped pulley 614 is a distal end of a contracting EAP fiber actuator 616 that follows the contour thereof and passes into the proximal frame ground 606. The contracting EAP fiber actuator 616 may be sufficiently long so that, for even a small percentage contraction in a length a significant rotation may be achieved. It should be appreciated that a counter rotating mechanism may be incorporated on a left side of the depicted tang 608 on a similar but reversed mechanism formed on the other side of the EAP articulation joint 600.

Longitudinal Articulation Locking Mechanism for Pivoting Articulation Mechanism.

In FIGS. 20-27, a longitudinal EAP actuated articulation lock 700 is incorporated into a pivoting articulation joint 702 for a surgical instrument 704. For clarity, a single pivoting frame assembly 706 is depicted with a proximal frame ground 708 having distally extended upper and lower pivot tabs 710, 712 that are pivotally engaged to proximally directed upper and lower tangs 714, 716 of a distal frame ground 718 that is attached to an end effector 720. An upper inner hole 722 in the upper pivot tab 710 is aligned under an upper outer hole 724 in the upper tang 714, which are pivotally pinned together by upper pivot pin 726. A lower inner hole 728 in the lower pivot tab 712 is aligned above a lower outer hole 730 in the lower tang 716. Holes 728, 712 are pivotally pinned together by a lower pivot pin 732. Upper and lower moment arms 734, 736 extend distally respectively from the upper and lower pivot tabs 710, 712. The upper moment arm 734 may be urged to the left toward an upper left attachment point 738 formed in the distal frame ground 718 by a generally horizontal upper left EAP fiber actuator 740. The upper moment arm 734 may be urged to the right toward an upper right attachment point 742 formed in the distal frame ground 718 by a generally horizontal upper right EAP fiber actuator 744. The lower moment arm 736 may be urged to the left toward a lower left attachment point 746 formed in the distal frame ground 718 by a generally horizontal lower left EAP fiber actuator 748. The lower moment arm 736 may be urged to the right toward a lower right attachment point 750 formed in the distal frame ground 718 by a generally horizontal lower right EAP fiber actuator 752.

Closure of the anvil 22 may occur by action of a closure mechanism that is not shown, such as an EAP actuator that acts upon the anvil pivot. Alternatively, a firing motion may first close the anvil prior to further motion effecting stapling and severing. As a further alternative, a closure sleeve assembly or other longitudinally coupled mechanism (not shown) may impart a closing motion to the anvil 22.

An upper EAP actuated articulation locking mechanism 800 advantageously unlocks the pivoting articulation joint 702 to allow articulating movement. The EAP actuated articulation locking mechanism 800 then relaxes to a locked state, providing a stable locked position that does not require power dissipation, and thus component heating, between changes in an amount of articulation. An upper locking bolt assembly 802 is shown in a rectangular upper lock recess 804 formed in the proximal frame ground 708 proximal to and vertically farther from the longitudinal centerline than the upper pivoting tab 710. A locking bolt 806 extends a locking tip 808 out of a distal slot 810, formed in the upper lock recess 804, into engagement in a nearest tooth root 812 of a gear segment 814 formed about a proximal surface about the upper pivot tang 714 of the distal frame ground 718. The locking bolt 806 proximally terminates in cross plate 816 that slides longitudinally in the rectangular upper lock recess 804 between the urging of a proximally positioned compression spring 818 and upper left and right EAP stack actuator 820, 822 that may be activated to expand longitudinally, compressing the compression spring 818 as the lock bolt 806 is moved proximally, thereby disengaging the locking tip 808 from the gear segment 814, allowing the pivoting articulation joint 702 to be repositioned. An upper lock cover 824 closes the upper lock recess 804.

Figure 23:
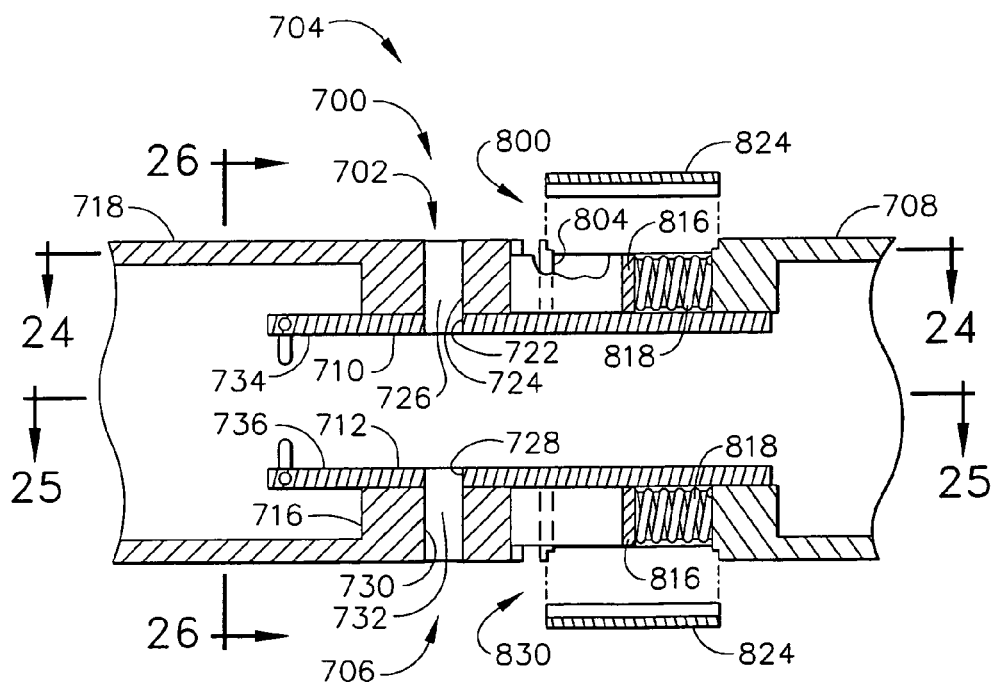
FIG. 23 is a right side view in elevation of the single pivot articulation joint of FIG. 22 taken in cross section along a longitudinal centerline of lines 23-23.
Figure 24:
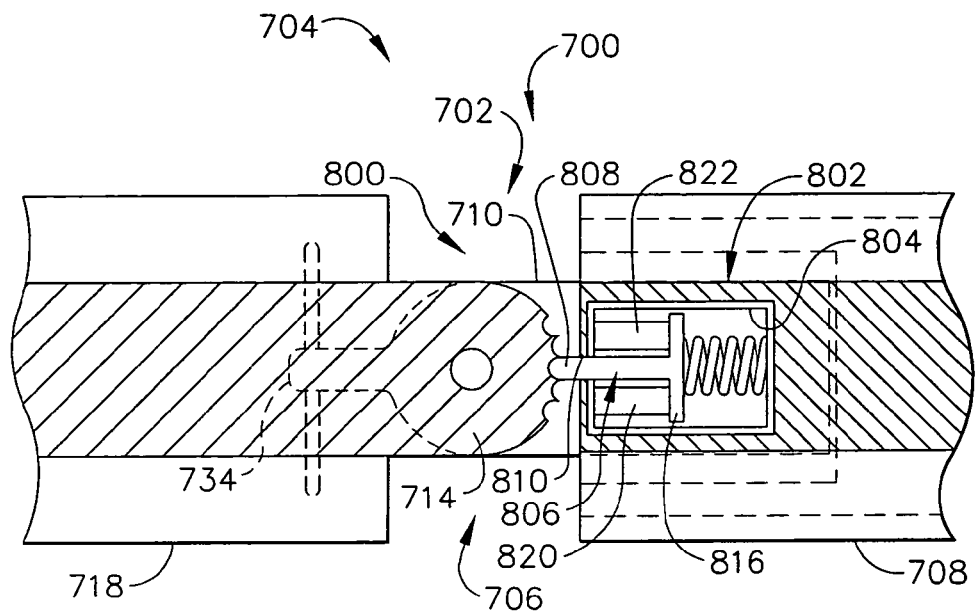
FIG. 24 is a top view of the single pivot articulation joint of FIG. 23 taken in cross section along lines 24-24 to show a gear segment on an upper pivot tang locked by the EAP articulation locking mechanism in an unarticulated condition.
Figure 25:
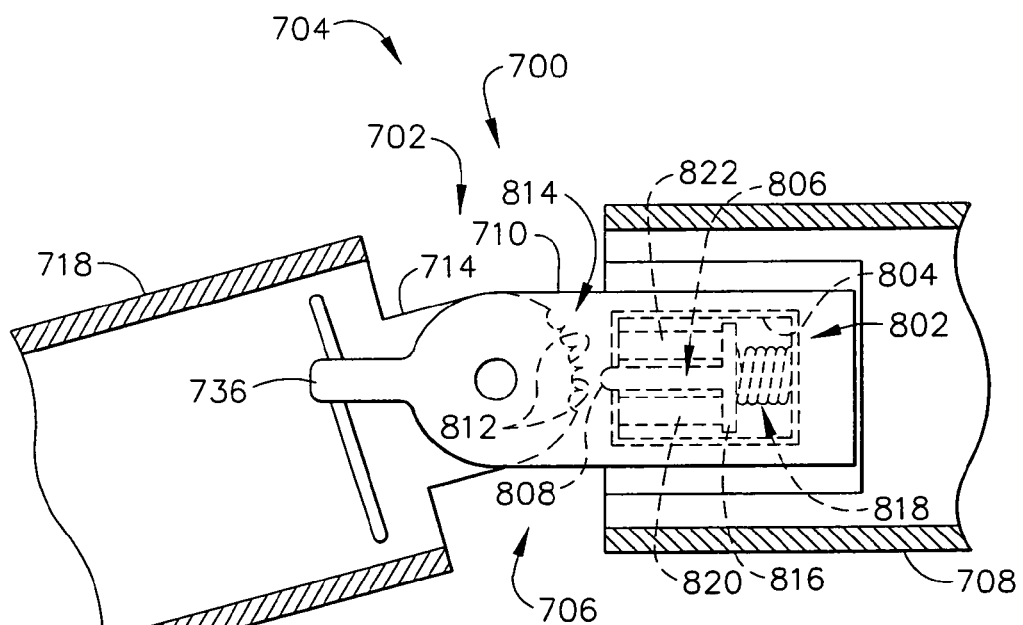
FIG. 25 is a top view of the single pivot articulation joint of FIG. 23 taken in cross section along a centerline of lines 25-25 looking down upon a lower pivot tab of a proximal frame ground that is partially articulating an end effector to the left while the EAP articulation locking mechanism is activated to an unlocked condition.
Figure 26:
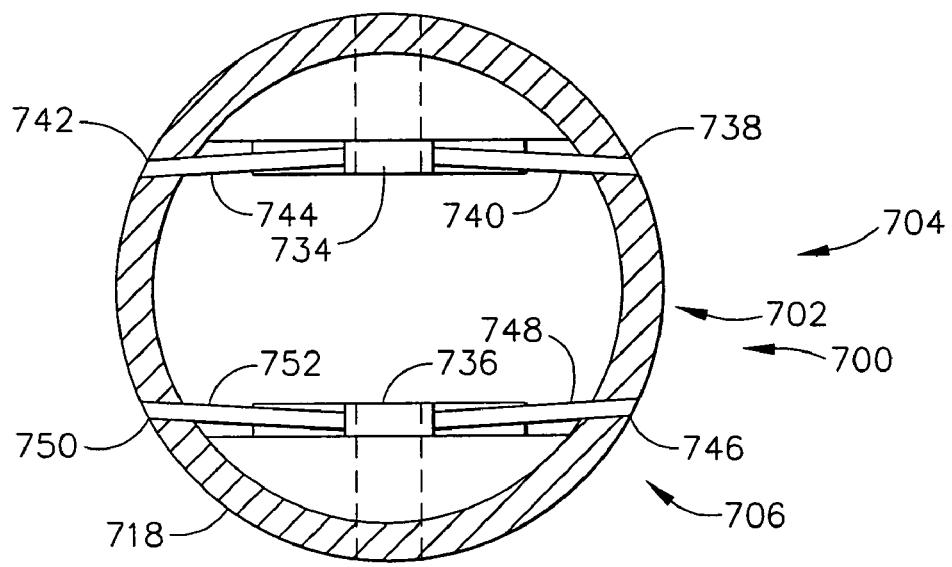
FIG. 26 is a front view in elevation of a distal frame ground of the single pivot articulation mechanism of FIG. 24 taken in cross section along lines 26-26 depicting attachment of EAP fiber actuators that articulate the joint.
Figure 27:
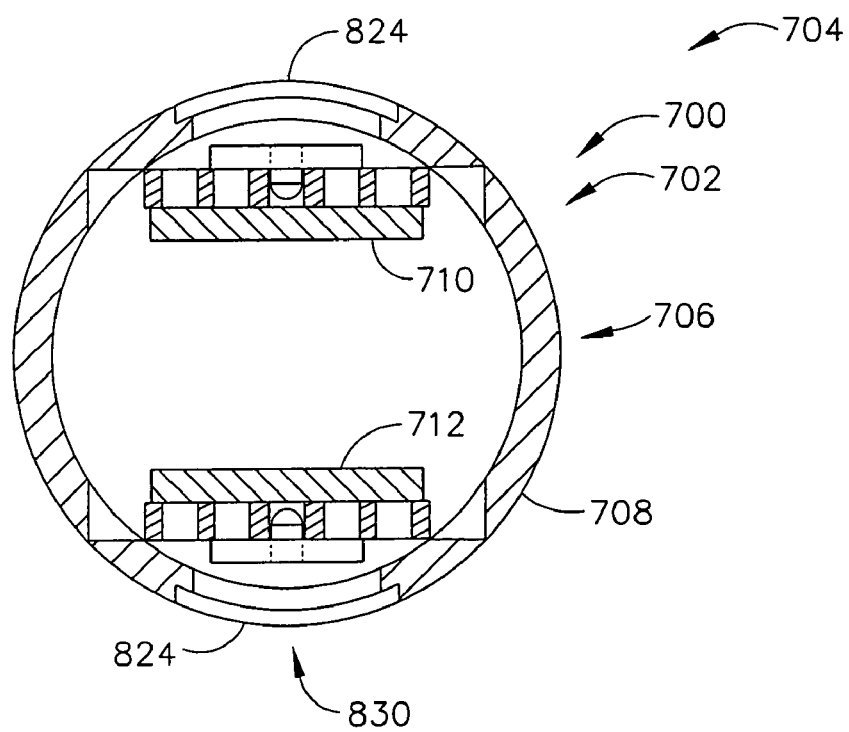
FIG. 27 is a front view in elevation of the proximal frame ground of the single pivot articulation joint of FIG. 24 taken in cross section along lines 27-27 to expose EAP stack actuators and locking pins of the EAP actuated locking mechanisms.

For additional locking support, in FIG. 23, a lower EAP actuated articulation locking mechanism 830, that is identical to the upper locking mechanism 800, acts on the opposite site against lower pivot tang 716. It should further be appreciated that a similar locking mechanism may be incorporated into a distal portion of an elongate shaft rather than a proximal end. Further, a double pivoting coupling may include a lock at each pivot.

In use, an unarticulated end effector 720 and pivoting articulation joint 702 (FIGS. 20-24) are inserted to a surgical site. With EAP locking mechanisms 800, 830 typically deenergized, the locking tip 808 attached to the proximal frame ground 708 engages the gear segment 814 of the distal frame ground 718, locking the single pivot frame assembly 706. When desired, EAP stack actuators 820, 822 are energized to longitudinally lengthen, unlocking the EAP articulation locking mechanisms 800, 830. While unlocked, the articulation joint 702 may be articulated, such as by contracting upper and lower right EAP fiber actuators 744, 752 to pivot the end effector 720 to the left (FIG. 25), presenting a different tooth root 812 to the locking tip 808 so that when deenergized the EAP articulation locking mechanism 800 will lock to the articulation condition of the surgical instrument 704.

Figure 28:
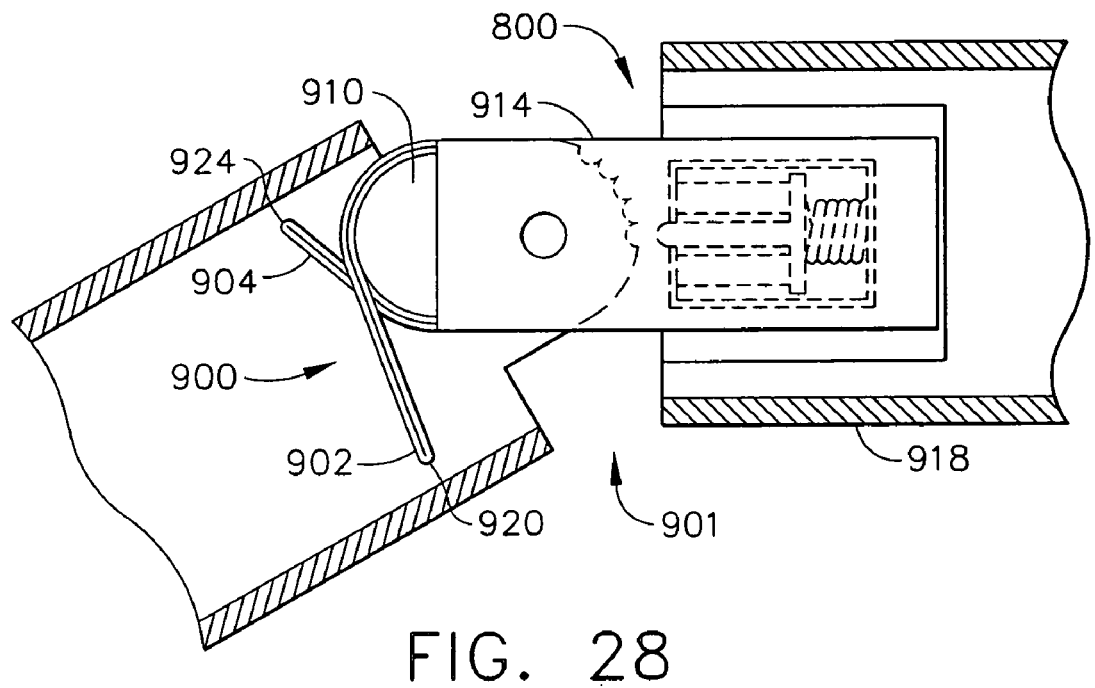
FIG. 28 is a top view taken in cross section along an interface between an upper pivot tang of a distal frame ground and an upper pivot tab of a proximal frame ground of a single pivot articulation joint advantageously incorporating lengthened EAP fiber actuators acting upon rounded moment arms in combination with the EAP articulation locking mechanism.
Figure 29:
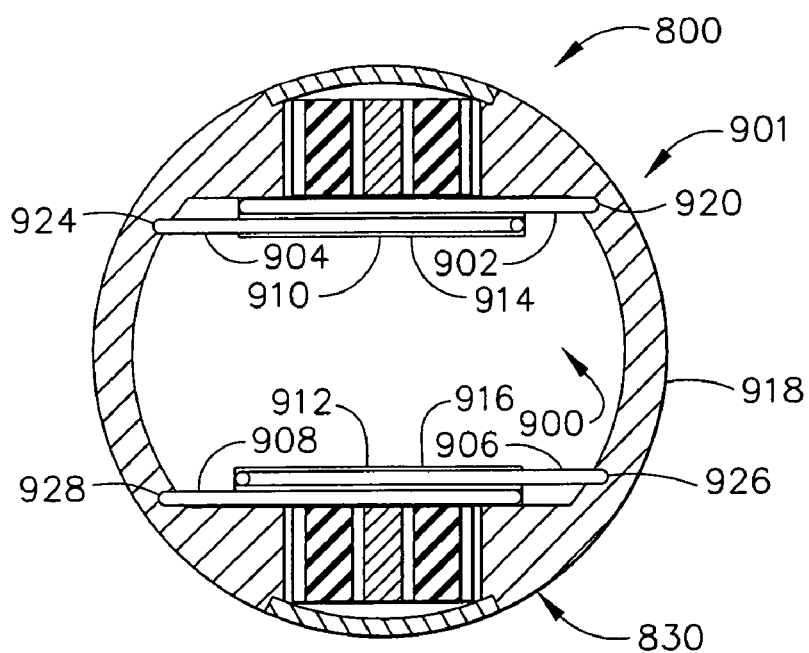
FIG. 29 is a front view in elevation taken generally in cross section through the proximal frame ground and EAP articulation locking mechanism but also showing more distally viewed moment arms and lengthened EAP fiber actuators connected thereto.

In FIGS. 28-29, an alternative EAP articulation system 900 for a single pivot articulation joint 901 is depicted for use in conjunction with the EAP articulation locking mechanism 800 previously described. Upper and lower pairs of left and right EAP fiber actuators 902, 904, 906, 908 are lengthened by incorporating upper and lower rounded moment arms 910, 912 distally respectively on upper and lower pivot tabs 914, 916 of a proximal frame ground 918. An upper left attachment point 920 in a distal frame ground 922 is slightly higher than an upper right attachment point 924. A lower left attachment point 926 is also slightly higher than a lower right attachment point 928, corresponding to the upper and lower left EAP fiber actuators 902, 906 wrapping respectively around a higher portion of the corresponding upper and lower rounded moment arms 910, 912 than the upper and lower right EAP fiber actuators 904, 908 (FIG. 29). Thereby, the lengthened EAP fiber actuators 902-908 in combination with the length and contour of the moment arms 910, 912 may be selected for a desired performance characteristic.

In FIGS. 30-33, an additional alternative EAP articulation system 1000 for a single pivot articulation joint 1001 is depicted for use in conjunction with the EAP articulation locking mechanism 800 previously described. Instead of EAP fiber actuators that effect articulation, upper and lower pairs of left and right EAP stack actuators 1002, 1004, 1006, 1008 respectively oppose and laterally move upper and lower longitudinal tracks 1010, 1012. A distally projecting upper moment arm 1014 attaches to an upper pivot tab 1016 of a proximal frame ground 1018. An upper inwardly directed tip pin 1020 at a distal end of the upper moment arm 1014 longitudinally slidingly engages the upper longitudinal track 1010, and thus responds to the differential contraction and expansion of the upper left and right EAP stack actuators 1002, 1004 that are laterally constrained by a distal frame ground 1022. A distally projecting lower moment arm 1024 attaches to an upper pivot tab 1026 of the proximal frame ground 1018. A lower inwardly directed tip pin 1030 at a distal end of the upper moment arm 1024 longitudinally slidingly engages the lower longitudinal track 1012, and thus responds to the differential contraction and expansion of the lower left and right EAP stack actuators 1006, 1008 that are laterally constrained by the distal frame ground 1022.

Figure 30:
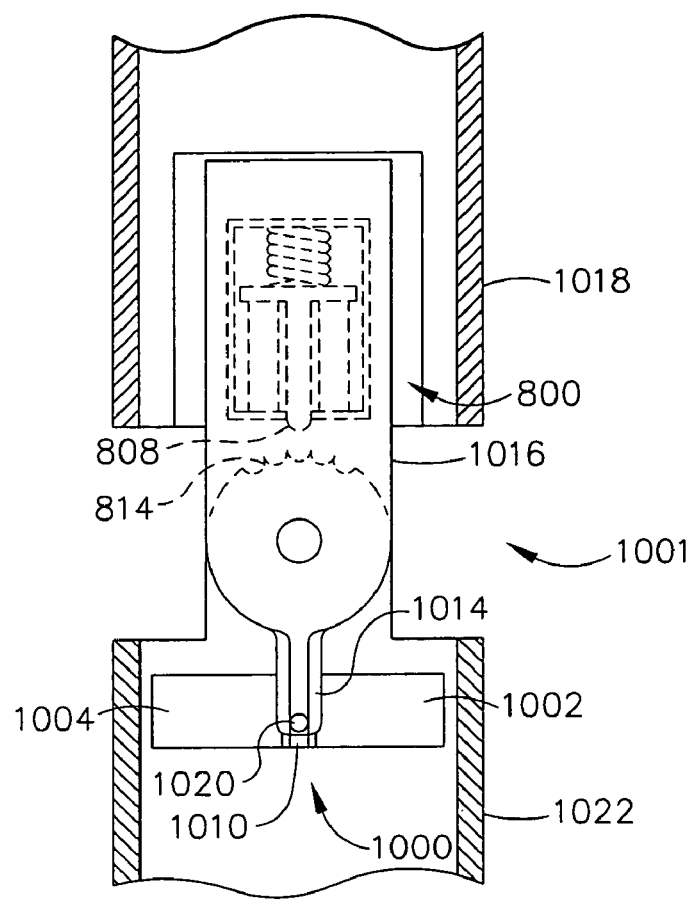
FIG. 30 is a top view of a single pivot articulation joint taken in cross section along a top surface of an upper pivot tab of a proximal frame ground to illustrate expansive EAP stack actuators employed against a moment arm distally attached to the upper pivot tab to effect articulation used in conjunction with the normally locked EAP articulation locking mechanism activated in preparation for articulation.
Figure 31:
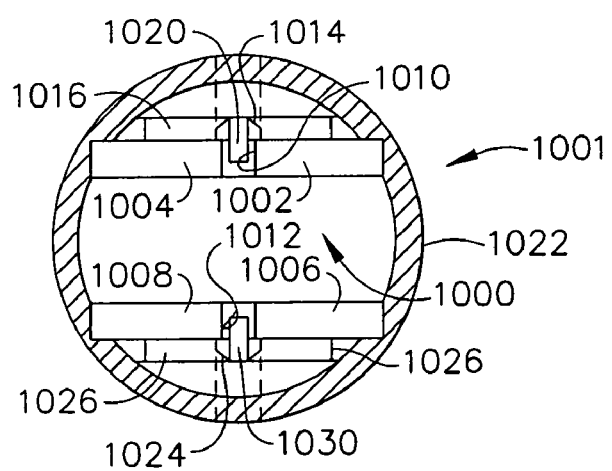
FIG. 31 is a front view in elevation of the single pivot articulation joint of FIG. 30 taken in cross section through upper and lower tip pins from the moment arms and through the EAP stack actuators.
Figure 32:
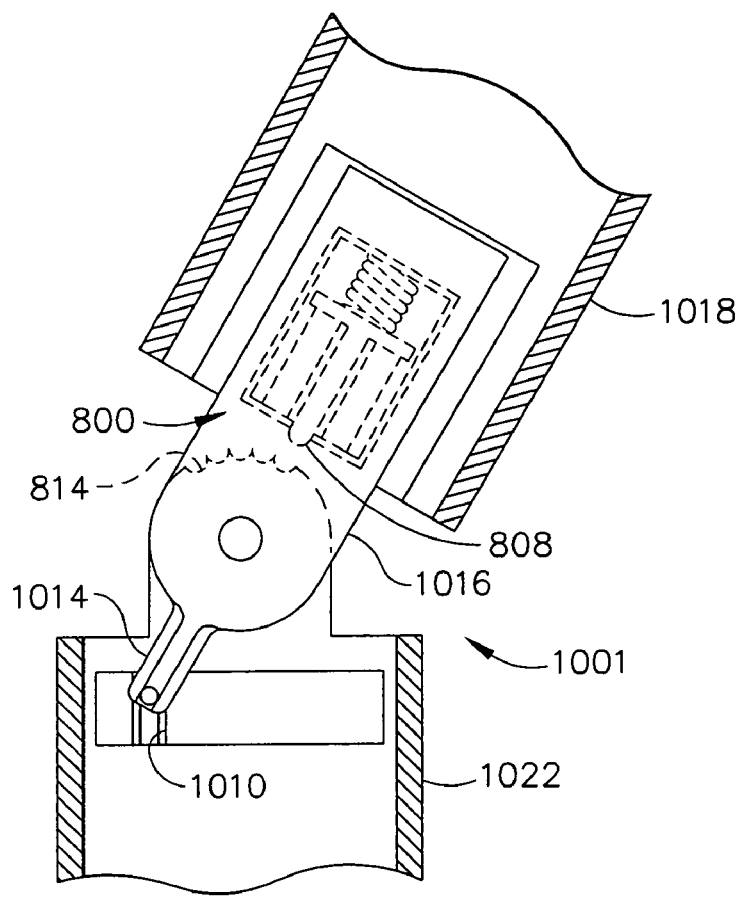
FIG. 32 is a top view of the single pivot articulation joint of FIG. 30 taken in cross section along a top surface of the upper pivot tab of the proximal frame ground after articulation of the distal frame ground to the left but before deenergizing the EAP articulation locking mechanism to effect articulation locking.
Figure 33:
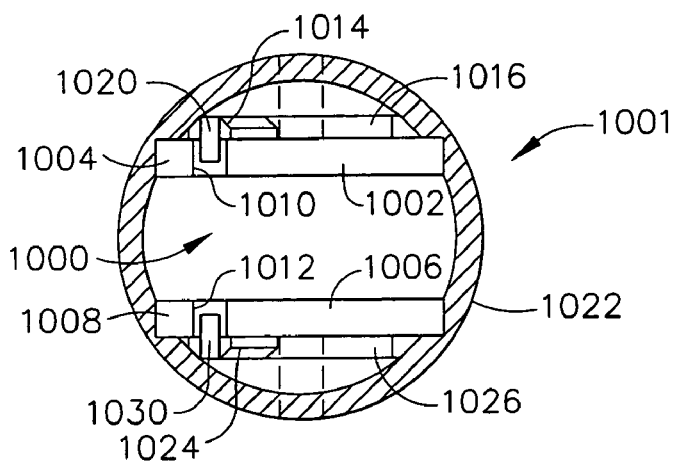
FIG. 33 is a front view in elevation of the single pivot articulation joint of FIG. 31 taken in cross section through the upper and lower tip pins from the moment arms and through the expanded left and compressed right EAP stack actuators.

In FIGS. 30-31, the EAP articulation locking mechanism 800 is activated to disengage the locking tip 808 from the gear segment 814 in preparation for articulation. In FIGS. 32-33, the upper and lower left EAP stack actuators 1002, 1006 have been energized to expand, laterally moving rightward the upper and lower longitudinal tracks 1010, 1012, thereby compressing the upper and lower EAP stack actuators 1004, 1008 and moving distal frame ground 1022 correspondingly against the reaction force from the upper and lower inwardly directed tip pins 1020, 1030, which in the illustrative articulation is to the left.

Surgical Instrument with EAP Actuated Flexneck Articulation Joint.

Figure 34:
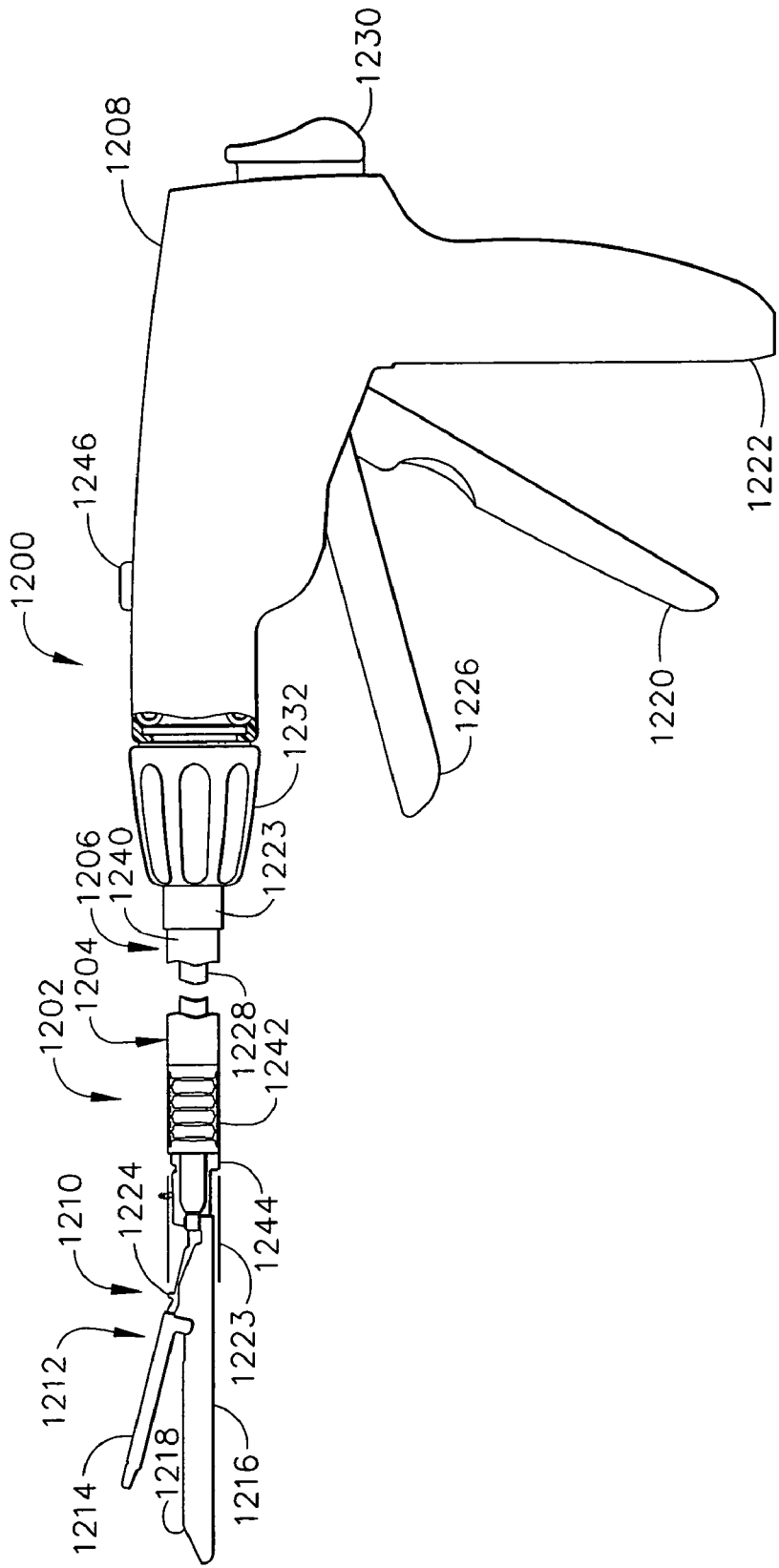
FIG. 34 is a right side view in elevation of a surgical instrument with a closure sleeve assembly cutaway to expose an EAP actuated articulation mechanism that articulates a flexible articulating frame ground.

In FIG. 34, a surgical instrument 1200 advantageously incorporates an EAP actuated articulation joint 1202 that is integral to an articulating frame assembly 1204 of an elongate shaft 1206 that transfers separate closure and firing motions from a handle 1208 to an end effector 1210, depicted as a staple applying assembly 1212 having a closeable anvil 1214 that is pivotally attached to an elongate channel 1216 that holds a replaceable staple cartridge 1218. The handle 1208 includes a closure trigger 1220 that is squeezed proximally toward a pistol grip 1222 to effect closure of the anvil 1214. It should be appreciated that a closure sleeve assembly 1223 or other closure means (e.g., EAP actuated anvil, internal longitudinally translating member, etc.) that is not shown acts upon an anvil closure feature 1224 to effect opening and closing of the anvil 1214. Once closed and clamped, a more distal firing trigger 1226 is squeezed toward the pistol grip 1222 to effect firing of a firing member 1228 longitudinally down the elongate shaft 1206 to cause severing of tissue and stapling of the severed ends. Once the firing trigger 1226 is released, a closure release button 1230 is depressed along with a slight depression of the closure trigger 1220 to release clamping components followed by release of the closure trigger 1220 to open the anvil 1214 and allow release of the stapled and severed tissue. A rotation knob 1232 allows selective rotation about a longitudinal axis of the elongate shaft 1206.

Figure 35:
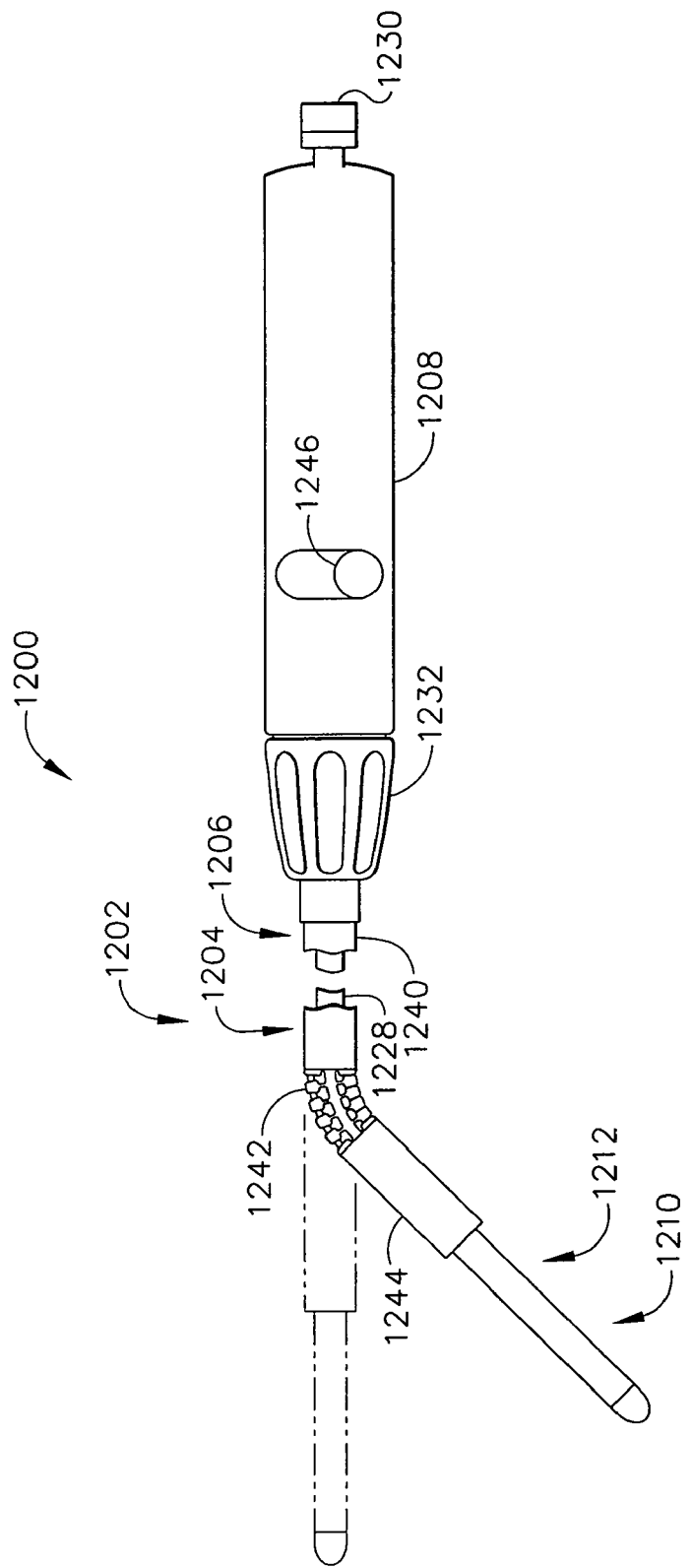
FIG. 35 is a top view of the surgical instrument of FIG. 34 articulating to the left.
Figure 36:
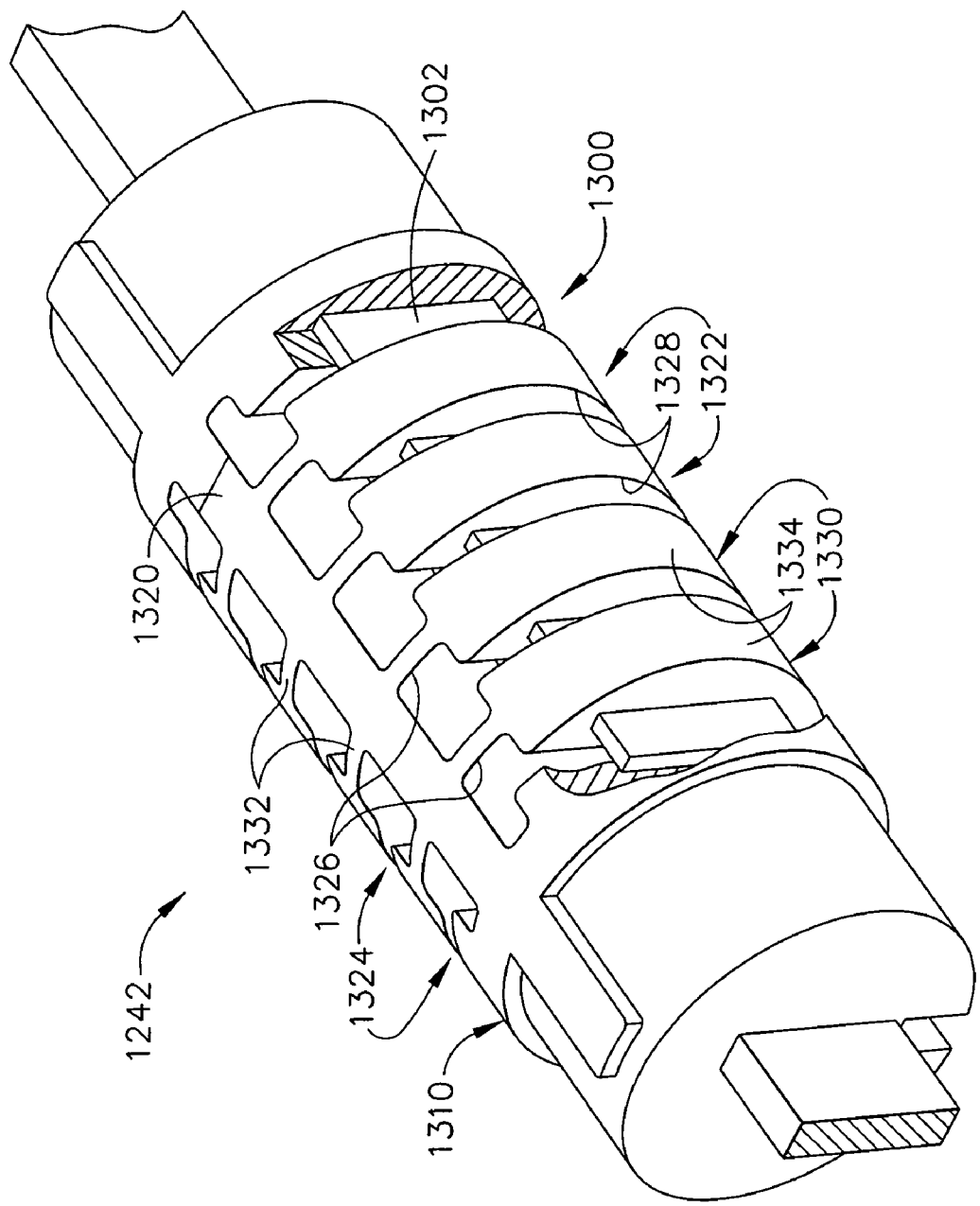
FIG. 36 is a front right perspective view of the articulating frame ground of FIG. 34 that incorporates EAP plate actuators and locking strips.

The articulating frame assembly 1204 includes a proximal frame ground 1240 proximally and rotatably attached to the handle 1208 and distally attached to an articulating frame ground 1242 that in turn is attached to a distal frame ground 1244 that supports the end effector 1210. An articulation control 1246 on the handle 1208 advantageously allows selection of articulation of the articulating frame ground 1242 by activating appropriate electrical signals thereto, such as depicted in FIG. 35 when a leftward articulation has been selected by articulation control 1246. It should be appreciated that the articulation control 1246 may advantageously include manual and/or automatic disengagement of an articulation lock for the articulating frame ground 1242.

In FIGS. 36-39, the articulating frame ground 1242 incorporates an EAP actuating system 1300 that uses left and right EAP plate actuators 1302, 1304 that pass through respective left and rectangular actuator recesses 1306, 1308 (FIGS. 38-39) in each lateral side of a generally cylindrical resilient frame body 1310. A rectangular knife slot 1312 is formed in the resilient frame body 1310 aligned between the left and right rectangular actuator recesses 1306, 1308 for guiding a firing bar 1314 that is a distal portion of the firing member 1228.

Figure 37:
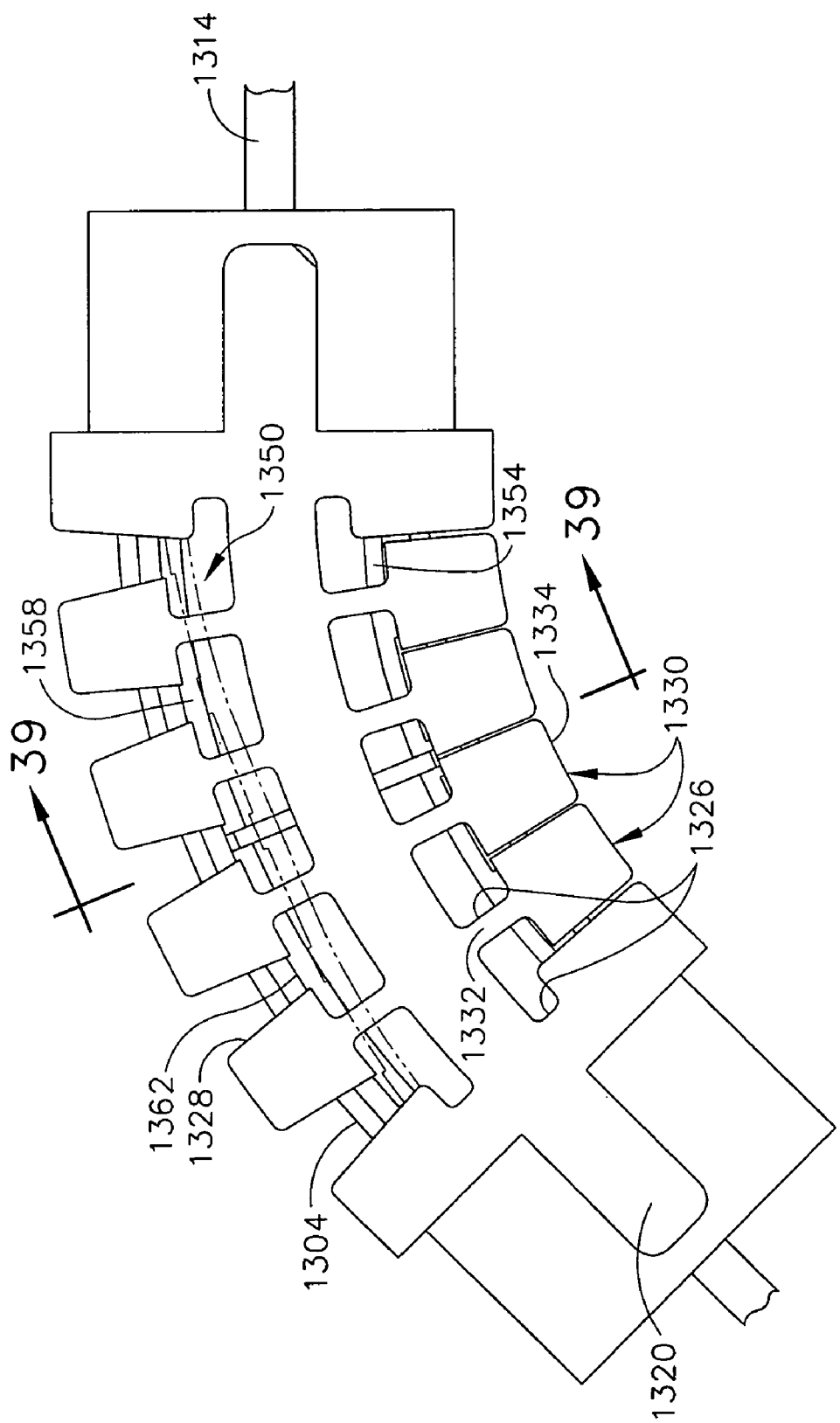
FIG. 37 is a top view of the articulating frame ground of FIG. 34 in a left articulated state with a left EAP locking strip shown in phantom in an unlocked actuated state and a locked relaxed state.

Continuous top and bottom longitudinal bands 1320 (FIGS. 36-37) of the resilient frame body 1310 maintain a longitudinal amount of travel for the firing bar 1314 when the articulating frame ground 1242 is either straight or articulated. The resilient frame body 1310 is advantageously formed from a homogenous material that does not significantly compress along its longitudinal axis. Left and right pluralities of longitudinally aligned vertical recesses 1322, 1324 intersect respectively with the left and right EAP actuator recesses 1306, 1308. Each vertical recess 1322, 1324 includes a rectangular through hole 1326 that passes from top to bottom through the resilient frame body 1310 parallel with and laterally offset from both the rectangular knife slot 1312 and the appropriate one of either the left or right rectangular actuator recess 1306, 1308. Each rectangular through hole 1326 communicates laterally with a narrowed lateral gap 1328. Adjacent vertical recesses 1322, 1324 define therebetween a rib 1330 that has a narrow inner wall 1332, which allows lateral bending of the continuous top and bottom longitudinal bands 1320, and a thicker curved outer slice 1334 that supports the respective one of the EAP plate actuators 1302, 1304 and limits the amount of articulation that may be achieved in that direction before the narrowed lateral gaps 1328 collapse fully as one or both EAP plate actuators 1302, 1304 are activated to bend in a selected direction. In FIG. 37, for instance, the left EAP plate actuator 1302 is activated to actuate to the left with the right EAP plate actuator 1304 stretching in response. It should be appreciated that the left and right EAP plate actuators 1302, 1304 may alternatively contract or expand when electrically activated to create a pull or a push respectively within the left and right rectangular actuator recesses 1306, 1308.

Figure 38:
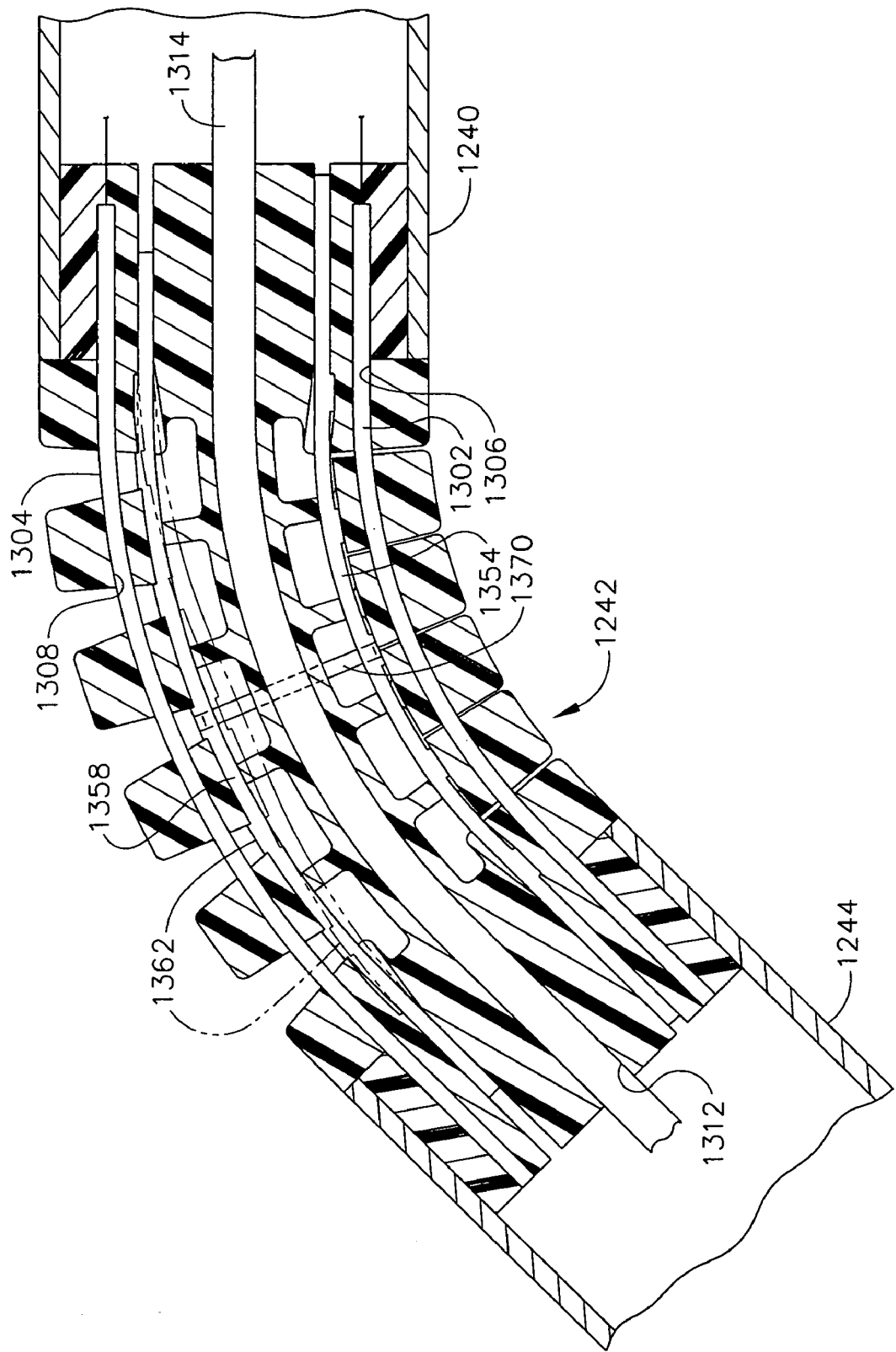
FIG. 38 is a top view of the articulating frame ground of FIG. 34 in a left articulated state taken in cross section through the EAP plate actuators and EAP locking strips.
Figure 39:
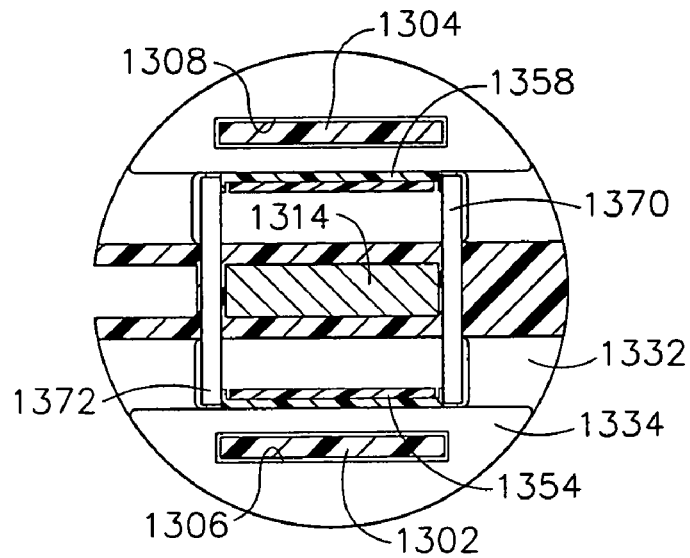
FIG. 39 is a front view in elevation of the articulating frame ground of FIG. 37 taken in cross section through lines 39-39 through the lateral guide pins.

In FIGS. 38-39, the articulating frame ground 1242 advantageously includes an EAP articulation locking mechanism 1350 that selectively holds the resilient frame body 1310 in an articulated left or an articulated right condition. To that end, a left locking passage 1352 is defined passing through the left plurality of rectangular through holes 1326 proximate to their leftmost outer portion, allowing a left ridged EAP locking strip 1354 to pass therethrough. Similarly, a right locking passage 1356 is defined as passing through the right plurality of rectangular through holes 1326 proximate to their rightmost outer portion, allowing placement of a right ridged EAP locking strip 1358. Along their respective outermost surface 1360 of both the left and right ridged EAP locking strips 1354, 1358, a plurality of longitudinally spaced vertical blocking ridges 1362 are longitudinally spaced and sized to define, in conjunction with the geometry of the ribs 1330 to lock at a desired articulation amount. In particular, when the flexible frame ground 1242 articulates toward the opposite side of a respective ridged EAP locking strip 1354, 1358, the ribs 1330 on that side arc away from one another, as depicted in FIG. 38 in articulating to the left. Once the ribs 1330 have reached a spacing sufficient for locking (i.e., wider than the longitudinal width of the vertical blocking ridges 1362), the right ridged EAP locking strip 1358 is biased outwardly to snap its ridges 1362 between adjacent thickened thicker curved outer slices 1334 of adjacent ribs 1330. Activating the right ridged EAP locking strip 1358 causes contraction that unlocks the right ridged EAP locking strip 1358. In FIG. 39, lateral upper and lower guide pins 1370, 1372, that pass above and below the rectangular knife slot 1312, preserve lateral alignment.

Figure 40:
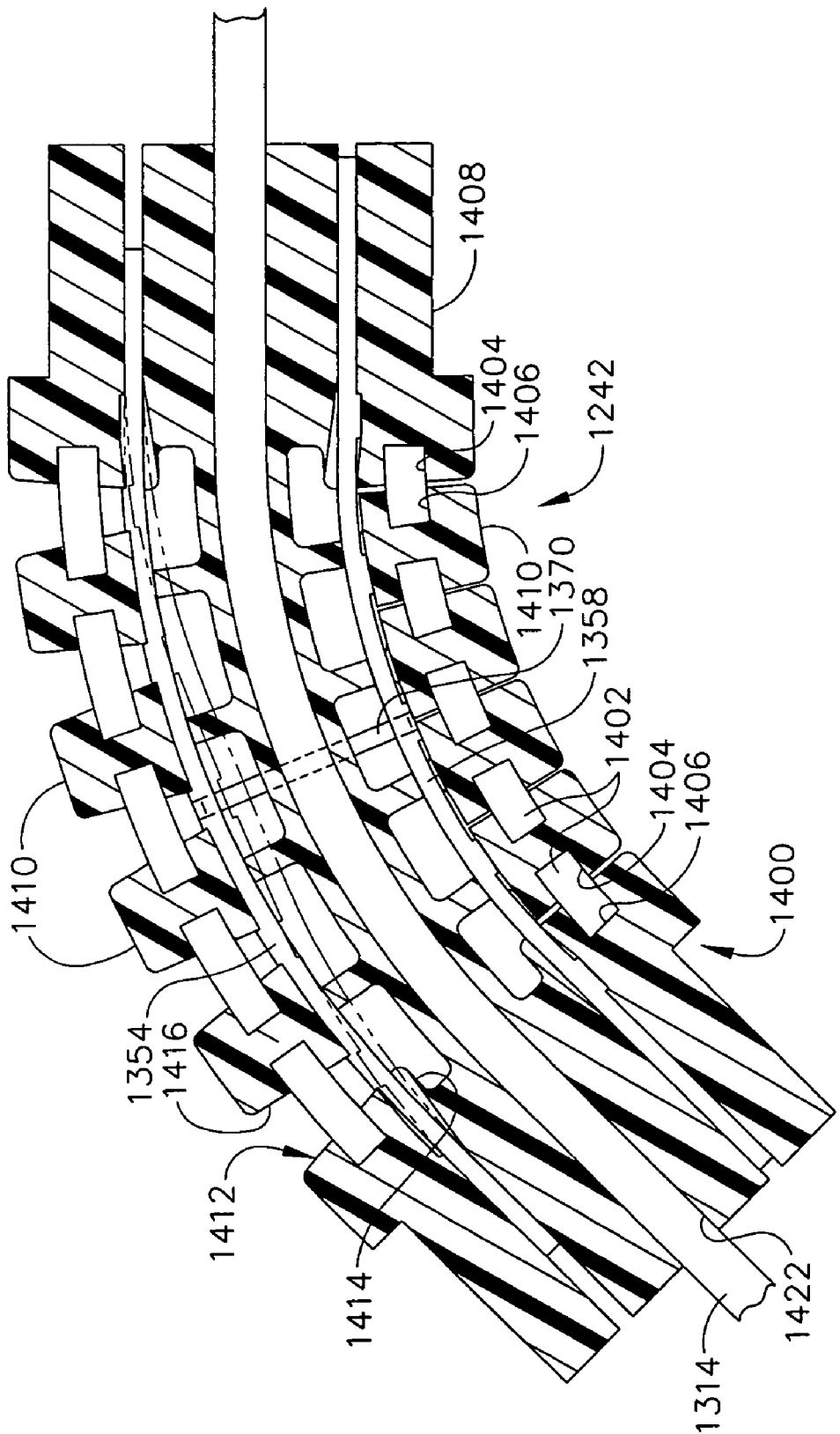
FIG. 40 is a top view of an alternate articulating frame ground taken in cross section through a plurality of EAP rib spreader actuators.

In FIG. 40, the articulating frame ground 1242 incorporates an EAP actuating system 1400 that uses a plurality of left and right EAP rib spreader plate actuators 1402 that each reside between an opposing pair of distally and proximally open rectangular recesses of a resilient frame body 1408. Each opposing pair of distally and proximally open rectangular actuator recesses 1404, 1406 respectively are formed in an adjacent pair (proximal/distal) of laterally defined ribs 1410. Each rib 1410 includes a vertical slot 1412 that is open outwardly laterally along its height with a wider rectangular through hole 1414 more inwardly positioned that narrows into an outer vertical slot 1416. Each rib 1410 thus includes a thin inner wall 1418 that connects to upper and lower longitudinal continuous bands 1420. A rectangular knife slot 1422 is formed laterally along the longitudinal centerline. Left and right ridged EAP locking strips 1354, 1358, as described above, advantageously relax to an expanded curved shape on the expanded side of the articulating frame ground 1242 to lock, with longitudinal alignment maintained by lateral guide pins 1370.

Figure 42:
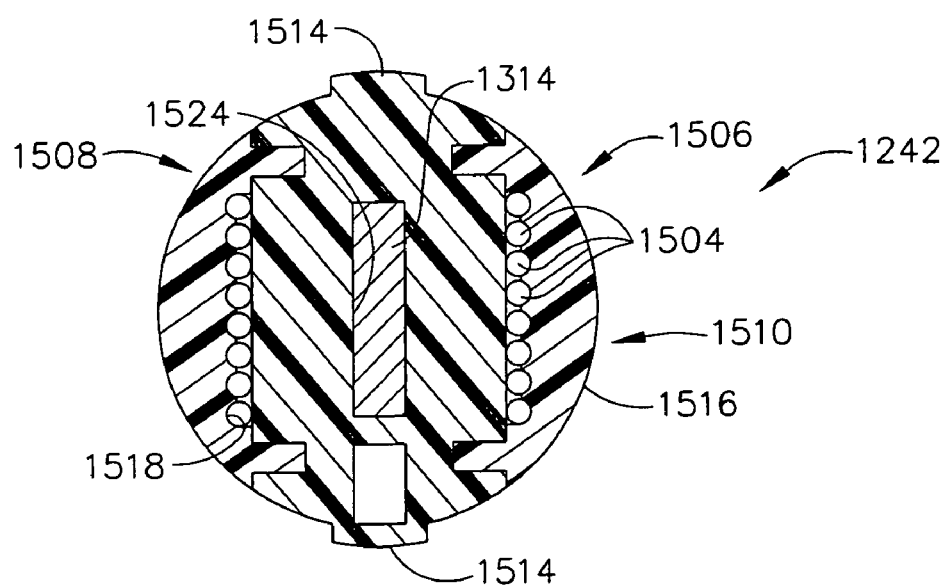
FIG. 42 is a front view in elevation of the additional alternative articulating frame ground of FIG. 41 taken in cross section along lines 42-42.
Figure 41:
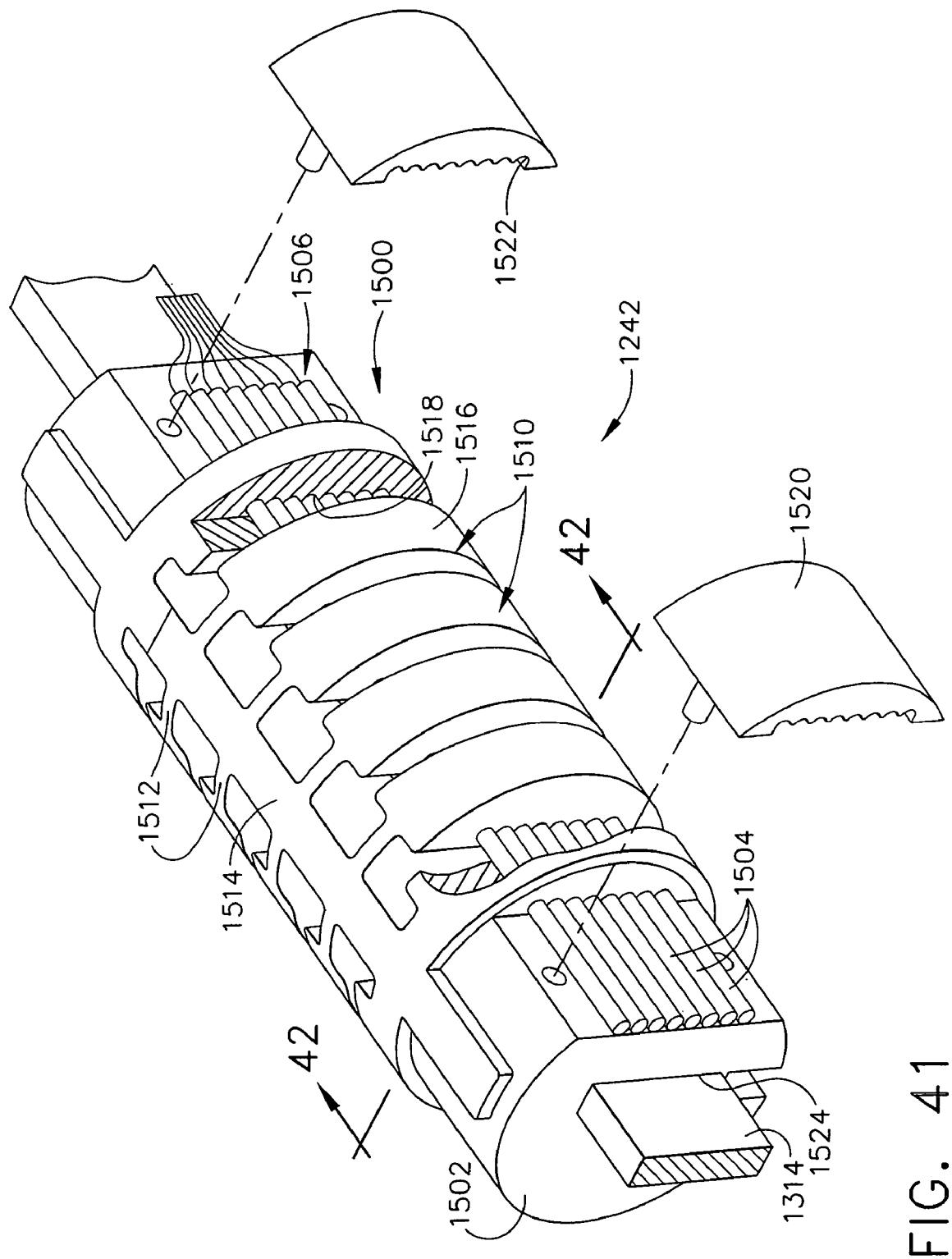
FIG. 41 is a right perspective partially exploded view of an additional alternative articulating frame ground having a plurality of EAP fiber actuators.

In FIGS. 41-42, the articulating frame ground 1242 incorporates a further alternative EAP actuating system 1500 into a resilient frame body 1502 that includes longitudinally aligned EAP fiber actuators 1504 arranged in left and right vertical stacks 1506, 1508 that pass through a respectively left and right plurality of lateral ribs 1510, each having a thin inner vertical wall 1512 that connects to continuous longitudinal top and bottom bands 1514 to facilitate lateral bending thereof. Each rib 1510 widens laterally to a thick outer slice 1516 that is dimensioned for the limitation on articulation to that side. Each thick outer slice 1516 includes a vertical aligned longitudinal through hole 1518 for allowing the EAP fiber actuators 1504 to pass through. Distal and proximal lateral covers 1520, 1522 longitudinally flank the ribs 1510 to cover respective termination ends of the EAP fiber actuators 1504. A laterally centered knife slot 1524 is formed in the resilient frame body 1502 for the firing bar 1314. Contracting a selected vertical stack 1506, 1508 of EAP fiber actuators 1504 causes articulation to that side with the nonactuated vertical stack 1506, 1508 passively elongating in response thereto.

Transverse Articulation Locking Mechanism for Pivoting Articulation Mechanism.

Figure 43:
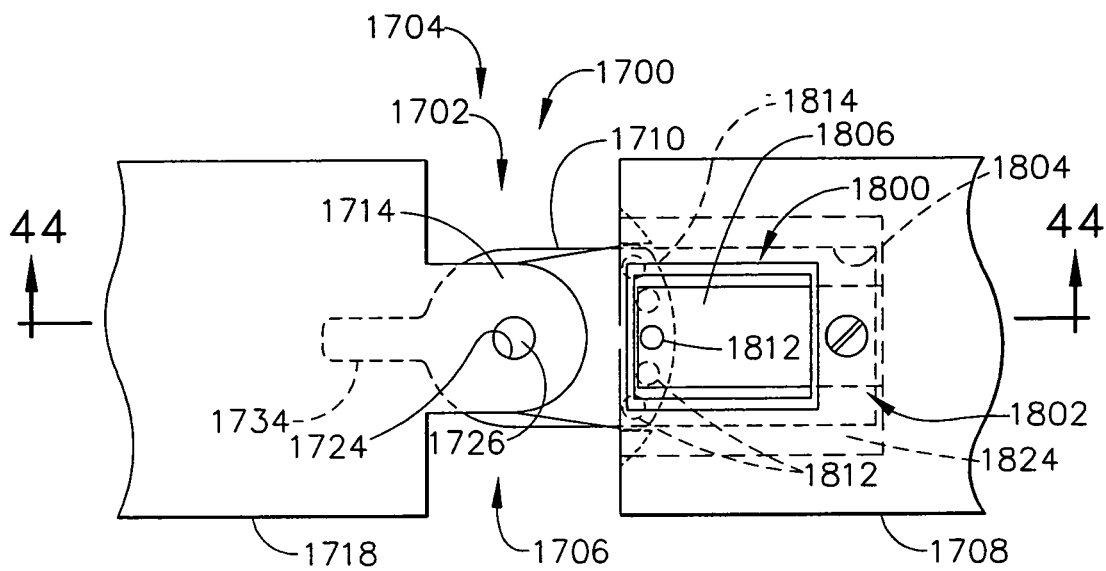
FIG. 43 is a top view of an alternative single pivot articulation joint with a transverse EAP articulation locking mechanism for the surgical instrument of FIG. 1.
Figure 44:
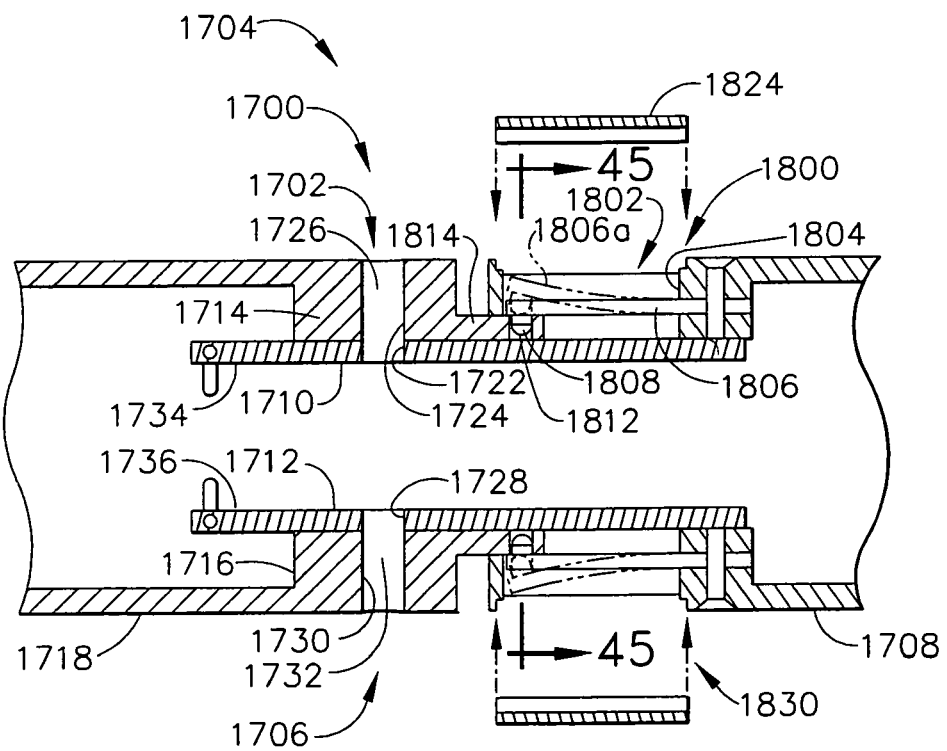
FIG. 44 is a side view in elevation of the alternative pivot articulation joint of FIG. 43 taken in cross section along a longitudinal centerline of lines 44-44.
Figure 45:
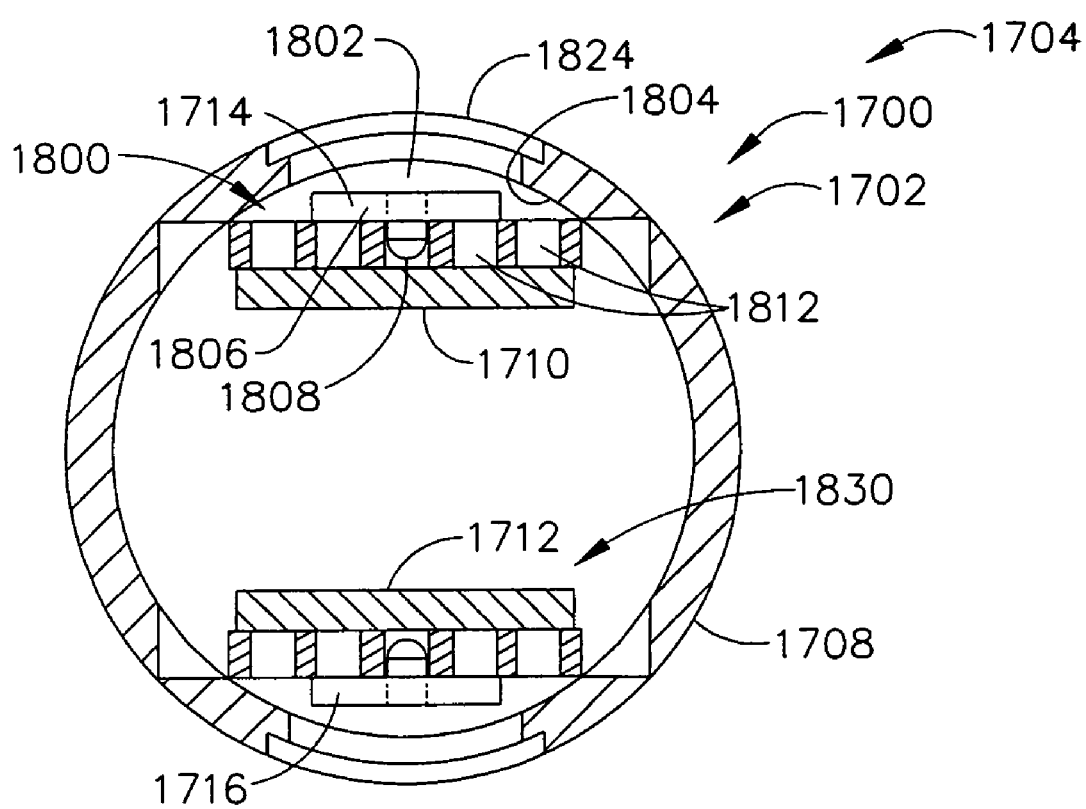
FIG. 45 is a front view in elevation of the alternative pivot articulation joint of FIG. 44 taken in cross section along transverse lines 45-45.

In FIGS. 43-45, a transverse EAP actuated articulation lock 1700 is incorporated into a pivoting articulation joint 1702 for a surgical instrument 1704. For clarity, a single pivoting frame assembly 1706 is depicted with a proximal frame ground 1708 having distally extended upper and lower pivot tabs 1710, 1712 that are pivotally engaged to proximally directed upper and lower tangs 1714, 1716 of a distal frame ground 1718 that is attached to an end effector (not shown in FIGS. 43-45). An upper inner hole 1722 in the upper pivot tab 1710 is aligned under an upper outer hole 1724 in the upper tang 1714, which are pivotally pinned together by upper pivot pin 1726. A lower inner hole 1728 in the lower pivot tab 1712 is aligned above a lower outer hole 1730 in the lower tang 1716. Holes 1728, 1712 are pivotally pinned together by a lower pivot pin 1732. Upper and lower moment arms 1734, 1736 extend distally respectively from the upper and lower pivot tabs 1710, 1712, urged laterally by EAP fiber actuators (not shown) as described above regarding FIGS. 20-27.

An upper EAP actuated articulation locking mechanism 1800 advantageously unlocks the pivoting articulation joint 1702 to allow articulating movement. The EAP actuated articulation locking mechanism 1800 then relaxes to a locked state, providing a stable locked position that does not require power dissipation, and thus component heating, between changes in an amount of articulation. An upper locking hook assembly 1802 is shown in a rectangular upper lock recess 1804 formed in the proximal frame ground 1708 proximal to and vertically farther from the longitudinal centerline than the upper pivoting tab 1710. An EAP locking hook latch 1806 originates at its proximal end within an upper horizontal slot 1807 formed in the proximal frame ground 1708 communicating with the proximal end of the rectangular upper lock recess 1804. An upper vertical pin passes through the proximal frame ground 1708, the upper horizontal slot 1807 constraining the proximal end of the upper EAP locking hook latch 1806 therein. The upper EAP locking hook latch 1806 is formed of an EAP plate actuator that is configured to bend its distal end upwardly and outwardly, as shown in phantom at 1806a in FIG. 44, pulling an inwardly directed locking tip 1808 out of a nearest peripherally spaced through hole 1812 in a rounded locking plate 1814. The rounded locking plate 1814 is formed about a proximal surface about the upper pivot tang 1714 of the distal frame ground 1718 which rotates under a distal portion of the upper lock recess 1804. An upper lock cover 1824 closes the upper lock recess 1804.

For additional locking support, in FIGS. 43-44, a lower EAP actuated articulation locking mechanism 1830, that is identical to the upper locking mechanism 1800, acts on the opposite site against lower pivot tang 1716. It should further be appreciated that a similar locking mechanism may be incorporated into a distal portion of an elongate shaft rather than a proximal end. Further, a double pivoting coupling may include a lock at each pivot.

In use, distal frame portion 718 and pivoting articulation joint 1702 (FIGS. 43-44) are inserted through a cannula to a surgical site. With EAP locking mechanisms 1800, 1830 typically deenergized, the locking tip 1808 attached to the proximal frame ground 1708 engages the center through hole 1814 of the distal frame ground 1718, locking the single pivot frame assembly 1706. When desired, the EAP locking hook latches 1806 are energized to bend outwardly within the lock recesses 1804, unlocking the EAP articulation locking mechanisms 1800, 1830. While unlocked, the articulation joint 1702 may be articulated, such as by actuating a mechanical linkage or EAP actuator. When articulated to the desired angle, the EAP articulation locking mechanisms 1800, 1830 are deenergized and thereby locked.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

What is claimed is:

1. A surgical instrument, comprising:
   an end effector;
   a handle portion comprising an articulation control and a locking control circuitry operably configured to produce an unlocking signal;
   an elongate shaft rotatable relative to the handle portion;
   an articulation mechanism comprising:
   a proximal frame portion attached to the elongate shaft,
   a distal frame portion attached to the end effector and rotatably coupled to the proximal frame portion to form an articulation joint, and
   an articulation actuator responsive to the articulation control of the handle portion and coupled between the proximal and distal frame portions and operably configured to effect articulation therebetween; and
   an electrical locking mechanism positioned between the handle and the end effector and movably engageable between the proximal and distal frame portions to lock the end effector at an angle relative to the elongate shaft by locking the articulation joint, wherein the electrical locking mechanism comprises:
   a locking member attached to the proximal frame portion or the distal frame portion, wherein the locking member is biased to extend toward and engage the other one of the proximal frame portion or the distal frame portion to lock the articulation joint, wherein the locking mechanism further comprises a resilient member resiliently biasing the locking member to extend toward and engage the other one of the proximal frame portion or the distal frame portion to lock the articulation joint, wherein the locking member is located at the articulation joint, and
   an electroactive polymer actuator coupled with the locking member, wherein the electroactive polymer actuator is operatively configured and positioned to overcome the bias on the locking member and move the locking member when activated by the unlocking signal to unlock the articulation joint.

2. The surgical instrument of claim 1, wherein the articulation control comprises circuitry operably configured to produce an articulation electrical signal, the articulation actuator comprising an electrical actuator responsive to the articulation electrical signal.

3. The surgical instrument of claim 1, wherein the proximal and distal frame portions of the articulation mechanism are pivotally attached to each other to form the articulation joint.

4. The surgical instrument of claim 3, wherein the elongate shaft further comprises a closure sleeve assembly, wherein the end effector comprises an upper jaw and a lower jaw, the articulation joint pivotally attaching the lower jaw of the end effector to a distal end of the distal frame portion, the handle portion operatively configured to longitudinally couple a closure motion to the closure sleeve assembly.

5. The surgical instrument of claim 3, wherein the articulation control comprises circuitry operably configured to produce an articulation electrical signal, the articulation actuator comprising an electrical actuator responsive to the articulation electrical signal.

6. The surgical instrument of claim 5, wherein a selected one of the proximal and distal frame portions present a moment arm pinned to the other one of the proximal and distal frame portions, the electrical actuator comprising a pair of electroactive polymer actuators opposingly coupled between the moment arm and the other of the proximal and distal frame portions to effect articulation.

* * * * *